US009724588B1

(12) United States Patent
Cronin et al.

(10) Patent No.: US 9,724,588 B1
(45) Date of Patent: Aug. 8, 2017

(54) PLAYER HIT SYSTEM

(71) Applicant: ProSports Technologies, LLC, Miami, FL (US)

(72) Inventors: John E. Cronin, Bonita Springs, FL (US); Nick Reasner, Chicago, IL (US); Maxx Thomas Garrison, Burlington, VT (US); Demaurice Fitzgerald Smith, Bethesda, MD (US); Ahmad E. Nassar, Vienna, VA (US)

(73) Assignee: PROSPORTS TECHNOLOGIES, LLC, Miami, FL (US)

( * ) Notice: Subject to any disclaimer, the term of this patent is extended or adjusted under 35 U.S.C. 154(b) by 0 days.

(21) Appl. No.: 14/798,068

(22) Filed: Jul. 13, 2015

Related U.S. Application Data

(60) Provisional application No. 62/023,588, filed on Jul. 11, 2014, provisional application No. 62/029,588, (Continued)

(51) Int. Cl.
*A63B 71/08* (2006.01)
*A63B 71/06* (2006.01)

(52) U.S. Cl.
CPC ...... *A63B 71/0619* (2013.01); *A63B 2220/00* (2013.01); *A63B 2220/05* (2013.01);
(Continued)

(58) Field of Classification Search
CPC ............ A63B 71/0619; A63B 71/0622; A63B 2071/0636; A63B 2071/0658; A63B 2071/0661; A63B 2071/0663; A63B 2071/0666; A63B 2220/00; A63B 2220/05; A63B 2220/50; A63B 2220/51; A63B 2220/53; A63B 2220/56; A63B 2220/80; A63B 2220/801; A63B 2220/833;
(Continued)

(56) References Cited

U.S. PATENT DOCUMENTS

| 4,763,284 | A | 8/1988 | Carlin |
| 4,771,394 | A | 9/1988 | Cavanagh |

(Continued)

FOREIGN PATENT DOCUMENTS

| AU | 2014100006 | 2/2014 |
| CN | 102527007 | 7/2012 |

(Continued)

OTHER PUBLICATIONS

U.S. Appl. No. 14/798,035, John E. Cronin, Playbook Processor, filed Jul. 13, 2015.
(Continued)

*Primary Examiner* — Damon Pierce
(74) *Attorney, Agent, or Firm* — Polsinelli LLP

(57) ABSTRACT

The systems and methods described herein are directed towards collecting and recording sensor data pertaining to physical contact experienced by players in a contact sport (e.g., football). The data can be collected and recorded through the use of one or more sensors worn by the player. In some cases, the sensor data can be associated with in-game video recordings of physical contact experienced by the players. Information about the physical contact can be displayed for users to view via a graphical user interface. Warnings may also be provided.

20 Claims, 15 Drawing Sheets

Related U.S. Application Data filed on Jul. 28, 2014, provisional application No. 62/029,624, filed on Jul. 28, 2014.

(52) U.S. Cl.
CPC ....... *A63B 2220/50* (2013.01); *A63B 2220/53* (2013.01); *A63B 2220/833* (2013.01); *A63B 2220/836* (2013.01)

(58) Field of Classification Search
CPC .......... A63B 2220/836; A63B 2230/00; A63B 2230/08; A63B 2230/085; A63B 22/00; A61B 5/11; A61B 5/1107; A61B 5/1112; A61B 5/1126; A61B 5/1127
See application file for complete search history.

(56) References Cited

U.S. PATENT DOCUMENTS

| | | |
|---|---|---|
| 5,293,354 A | 3/1994 | Costabile |
| 5,462,275 A | 10/1995 | Lowe et al. |
| 6,013,007 A | 1/2000 | Root et al. |
| 6,181,236 B1 | 1/2001 | Schneider |
| 6,389,368 B1 | 5/2002 | Hampton |
| 6,603,711 B2 | 8/2003 | Calace |
| 6,760,276 B1 | 7/2004 | Karr |
| 6,836,744 B1 | 12/2004 | Asphahani et al. |
| 7,020,336 B2 | 3/2006 | Cohen-Solal et al. |
| 7,031,225 B2 | 4/2006 | McDonald |
| 7,115,053 B2 | 10/2006 | Meichner |
| 7,173,533 B1 | 2/2007 | Beron et al. |
| 7,174,277 B2 | 2/2007 | Vock et al. |
| 7,561,494 B2 | 7/2009 | Stern |
| 7,561,723 B2 | 7/2009 | Goldberg et al. |
| 7,602,301 B1 | 10/2009 | Stirling et al. |
| 7,618,312 B1 | 11/2009 | Kasten |
| 7,634,662 B2 | 12/2009 | Monroe |
| 7,693,668 B2 | 4/2010 | Vock et al. |
| 7,715,723 B2 | 5/2010 | Kagawa et al. |
| 7,805,149 B2 | 9/2010 | Werner et al. |
| 7,920,052 B2 | 4/2011 | Costabile |
| 8,054,174 B1 | 11/2011 | Uehran |
| 8,098,881 B2 | 1/2012 | Camp et al. |
| 8,239,146 B2 | 8/2012 | Vock et al. |
| 8,253,586 B1 | 8/2012 | Matak |
| 8,257,084 B1 | 9/2012 | Kreiner et al. |
| 8,257,228 B2 | 9/2012 | Quatrochi et al. |
| 8,289,185 B2 | 10/2012 | Alonso |
| 8,326,136 B1 | 12/2012 | Clark |
| 8,396,687 B2 | 3/2013 | Vock et al. |
| 8,477,046 B2 | 7/2013 | Alonso |
| 8,485,879 B2 | 7/2013 | Lin et al. |
| 8,554,495 B2 | 10/2013 | Mack et al. |
| 8,554,509 B2 | 10/2013 | Crisco et al. |
| 8,579,632 B2 | 11/2013 | Crowley |
| 8,589,667 B2 | 11/2013 | Mujtaba et al. |
| 8,611,930 B2 | 12/2013 | Louboutin et al. |
| 8,620,344 B2 | 12/2013 | Huang et al. |
| 8,626,465 B2 | 1/2014 | Moore et al. |
| 8,630,216 B2 | 1/2014 | Deivasigamani et al. |
| 8,660,501 B2 | 2/2014 | Sanguinetti |
| 8,684,819 B2 | 4/2014 | Thomas et al. |
| 8,702,504 B1 | 4/2014 | Hughes et al. |
| 8,706,044 B2 | 4/2014 | Chang et al. |
| 8,724,723 B2 | 5/2014 | Panicker et al. |
| 8,750,207 B2 | 6/2014 | Jeong et al. |
| 8,793,094 B2 | 7/2014 | Tam et al. |
| 8,816,868 B2 | 8/2014 | Tan et al. |
| 8,831,529 B2 | 9/2014 | Toh et al. |
| 8,831,655 B2 | 9/2014 | Burchill et al. |
| 8,836,851 B2 | 9/2014 | Brunner |
| 8,843,158 B2 | 9/2014 | Nagaraj |
| 8,849,308 B2 | 9/2014 | Marti et al. |
| 8,862,060 B2 | 10/2014 | Mayor |
| 8,873,418 B2 | 10/2014 | Robinson et al. |
| 8,874,090 B2 | 10/2014 | Abuan et al. |
| 8,917,632 B2 | 12/2014 | Zhou et al. |
| 8,934,921 B2 | 1/2015 | Marti et al. |
| 8,994,498 B2 | 3/2015 | Agrafioti et al. |
| 9,305,441 B1 | 4/2016 | Cronin |
| 9,398,213 B1 | 7/2016 | Cronin |
| 9,474,933 B1 | 10/2016 | Cronin |
| 9,502,018 B2 | 11/2016 | Cronin |
| 9,610,491 B2 | 4/2017 | Cronin |
| 2001/0003715 A1 | 6/2001 | Jutzi et al. |
| 2001/0048484 A1 | 12/2001 | Tamir et al. |
| 2003/0163287 A1* | 8/2003 | Vock .................... A43B 3/0005 702/187 |
| 2003/0210612 A1 | 11/2003 | Stern |
| 2005/0046584 A1 | 3/2005 | Breed |
| 2005/0117022 A1 | 6/2005 | Marchant |
| 2005/0162257 A1 | 7/2005 | Gonzalez |
| 2005/0242508 A1 | 11/2005 | Meichner |
| 2005/0277466 A1 | 12/2005 | Lock |
| 2006/0052147 A1 | 3/2006 | Matthews |
| 2006/0074338 A1 | 4/2006 | Greenwald et al. |
| 2006/0109089 A1 | 5/2006 | Boehm et al. |
| 2006/0180073 A1 | 8/2006 | Nakamoto |
| 2006/0208169 A1 | 9/2006 | Breed et al. |
| 2006/0281061 A1 | 12/2006 | Hightower et al. |
| 2007/0003113 A1 | 1/2007 | Goldberg |
| 2007/0135264 A1 | 6/2007 | Rosenberg |
| 2007/0269203 A1 | 11/2007 | Awazu |
| 2008/0082311 A1 | 4/2008 | Meijer et al. |
| 2008/0129825 A1 | 6/2008 | DeAngelis et al. |
| 2008/0146302 A1 | 6/2008 | Olsen et al. |
| 2009/0023122 A1 | 1/2009 | Lieberman et al. |
| 2009/0029754 A1 | 1/2009 | Slocum et al. |
| 2009/0111582 A1 | 4/2009 | Schuler et al. |
| 2009/0256912 A1 | 10/2009 | Rosenberg |
| 2010/0026809 A1 | 2/2010 | Curry |
| 2010/0030350 A1 | 2/2010 | House et al. |
| 2010/0102938 A1 | 4/2010 | Delia et al. |
| 2010/0105503 A1 | 4/2010 | Daisher et al. |
| 2010/0144414 A1 | 6/2010 | Edis et al. |
| 2010/0185398 A1 | 7/2010 | Berns et al. |
| 2010/0283630 A1 | 11/2010 | Alonso |
| 2011/0013087 A1 | 1/2011 | House et al. |
| 2011/0064281 A1 | 3/2011 | Chan |
| 2011/0169959 A1 | 7/2011 | DeAngelis et al. |
| 2011/0181418 A1 | 7/2011 | Mack et al. |
| 2011/0184320 A1 | 7/2011 | Shipps et al. |
| 2011/0251802 A1 | 10/2011 | Song |
| 2012/0002509 A1 | 1/2012 | Saguin et al. |
| 2012/0029666 A1 | 2/2012 | Crowley et al. |
| 2012/0052947 A1 | 3/2012 | Yun |
| 2012/0063272 A1 | 3/2012 | Dorais et al. |
| 2012/0081531 A1 | 4/2012 | DeAngelis et al. |
| 2012/0099405 A1 | 4/2012 | Lidor et al. |
| 2012/0100911 A1 | 4/2012 | Rejen |
| 2012/0116259 A1 | 5/2012 | McConnell et al. |
| 2012/0116548 A1 | 5/2012 | Goree et al. |
| 2012/0120201 A1 | 5/2012 | Ward |
| 2012/0124720 A1 | 5/2012 | Evans et al. |
| 2012/0166449 A1 | 6/2012 | Pitaliya |
| 2012/0197998 A1 | 8/2012 | Kessel et al. |
| 2012/0202594 A1 | 8/2012 | Bistis et al. |
| 2012/0212505 A1 | 8/2012 | Burroughs et al. |
| 2012/0223833 A1 | 9/2012 | Thomas et al. |
| 2012/0324491 A1 | 12/2012 | Bathiche et al. |
| 2013/0018494 A1 | 1/2013 | Amini |
| 2013/0045806 A1 | 2/2013 | Bloodworth |
| 2013/0060168 A1 | 3/2013 | Chu et al. |
| 2013/0066448 A1 | 3/2013 | Alonso |
| 2013/0080222 A1 | 3/2013 | Quinn |
| 2013/0091209 A1 | 4/2013 | Bennett et al. |
| 2013/0095924 A1 | 4/2013 | Geisner et al. |
| 2013/0126713 A1 | 5/2013 | Haas et al. |
| 2013/0138590 A1 | 5/2013 | Huke et al. |
| 2013/0139068 A1 | 5/2013 | Bowring |
| 2013/0141555 A1 | 6/2013 | Ganick et al. |
| 2013/0166048 A1 | 6/2013 | Werner et al. |
| 2013/0222133 A1 | 8/2013 | Schultz et al. |
| 2013/0235702 A1 | 9/2013 | Saguin et al. |

(56) References Cited

U.S. PATENT DOCUMENTS

| | | |
|---|---|---|
| 2013/0249708 A1 | 9/2013 | Moll-Carrillo et al. |
| 2013/0279917 A1 | 10/2013 | Son et al. |
| 2013/0303192 A1 | 11/2013 | Louboutin |
| 2013/0314407 A1 | 11/2013 | Meehan |
| 2013/0316837 A1 | 11/2013 | Coiner, Jr. |
| 2013/0317835 A1 | 11/2013 | Mathew |
| 2013/0322689 A1 | 12/2013 | Carmichael |
| 2013/0324239 A1 | 12/2013 | Ur et al. |
| 2013/0328917 A1 | 12/2013 | Zambetti et al. |
| 2013/0331087 A1 | 12/2013 | Shoemaker |
| 2013/0331118 A1 | 12/2013 | Chhabra |
| 2013/0331137 A1 | 12/2013 | Burchill |
| 2013/0332108 A1 | 12/2013 | Patel |
| 2013/0332156 A1 | 12/2013 | Tackin |
| 2013/0335635 A1 | 12/2013 | Ghanem et al. |
| 2013/0336662 A1 | 12/2013 | Murayama et al. |
| 2013/0343762 A1 | 12/2013 | Murayama et al. |
| 2014/0004939 A1 | 1/2014 | Kasten |
| 2014/0039354 A1* | 2/2014 | Greenwald .......... A61B 5/0002 |
| | | 600/595 |
| 2014/0039355 A1 | 2/2014 | Crisco et al. |
| 2014/0039651 A1 | 2/2014 | Crowley |
| 2014/0062773 A1 | 3/2014 | MacGougan |
| 2014/0065962 A1 | 3/2014 | Le |
| 2014/0068847 A1* | 3/2014 | Kitowski ............. A41D 13/005 |
| | | 2/455 |
| 2014/0071221 A1 | 3/2014 | Dave |
| 2014/0080638 A1 | 3/2014 | Feng et al. |
| 2014/0088454 A1 | 3/2014 | Mack |
| 2014/0105084 A1 | 4/2014 | Chhabra |
| 2014/0105466 A1 | 4/2014 | Botes et al. |
| 2014/0107817 A1 | 4/2014 | Ellis et al. |
| 2014/0111352 A1 | 4/2014 | Doherty |
| 2014/0125702 A1 | 5/2014 | Santillan et al. |
| 2014/0139380 A1 | 5/2014 | Ouyang |
| 2014/0141803 A1 | 5/2014 | Marti |
| 2014/0143940 A1* | 5/2014 | Iuliano ................... A42B 3/046 |
| | | 2/422 |
| 2014/0155178 A1 | 6/2014 | Bloodworth |
| 2014/0162628 A1 | 6/2014 | Bevelacqua |
| 2014/0167794 A1 | 6/2014 | Nath |
| 2014/0168170 A1 | 6/2014 | Lazarescu |
| 2014/0168477 A1 | 6/2014 | David |
| 2014/0171114 A1 | 6/2014 | Marti |
| 2014/0180820 A1 | 6/2014 | Louboutin |
| 2014/0191979 A1 | 7/2014 | Tsudik |
| 2014/0200053 A1 | 7/2014 | Balasubramanian |
| 2014/0218184 A1 | 8/2014 | Grant et al. |
| 2014/0222335 A1 | 8/2014 | Piemonte |
| 2014/0232633 A1 | 8/2014 | Shultz |
| 2014/0232634 A1 | 8/2014 | Piemonte |
| 2014/0241730 A1 | 8/2014 | Jovicic |
| 2014/0247279 A1 | 9/2014 | Nicholas |
| 2014/0247280 A1 | 9/2014 | Nicholas |
| 2014/0269562 A1 | 9/2014 | Burchill |
| 2014/0270375 A1 | 9/2014 | Canavan et al. |
| 2014/0274150 A1 | 9/2014 | Marti |
| 2014/0278218 A1 | 9/2014 | Chang |
| 2014/0283135 A1 | 9/2014 | Shepherd |
| 2014/0293959 A1 | 10/2014 | Singh |
| 2014/0361906 A1 | 12/2014 | Hughes et al. |
| 2014/0363168 A1 | 12/2014 | Walker |
| 2014/0364089 A1 | 12/2014 | Lienhart |
| 2014/0364148 A1 | 12/2014 | Block |
| 2014/0365120 A1 | 12/2014 | Vulcano |
| 2014/0365194 A1 | 12/2014 | O'Hagan et al. |
| 2014/0365640 A1 | 12/2014 | Wohl et al. |
| 2014/0371887 A1 | 12/2014 | Hoffman et al. |
| 2014/0375217 A1 | 12/2014 | Feri et al. |
| 2015/0011242 A1 | 1/2015 | Nagaraj |
| 2015/0026623 A1 | 1/2015 | Horne et al. |
| 2015/0031397 A1 | 1/2015 | Jouaux |
| 2015/0081713 A1 | 3/2015 | Alonso et al. |
| 2015/0131845 A1 | 5/2015 | Forouhar et al. |
| 2015/0187188 A1 | 7/2015 | Raskin |
| 2015/0296272 A1 | 10/2015 | Sonabend et al. |
| 2015/0306457 A1 | 10/2015 | Crankson et al. |
| 2016/0001159 A1 | 1/2016 | Riley et al. |
| 2016/0008693 A1 | 1/2016 | Cronin |
| 2016/0012810 A1 | 1/2016 | Cronin |
| 2016/0018278 A1 | 1/2016 | Jeter |
| 2016/0073010 A1 | 3/2016 | Cronin |
| 2016/0096074 A1 | 4/2016 | Moll-Carrillo et al. |
| 2016/0107064 A1 | 4/2016 | Hoffman et al. |

FOREIGN PATENT DOCUMENTS

| | | |
|---|---|---|
| CN | 102843186 | 12/2012 |
| EP | 2 407 218 | 1/2012 |
| WO | WO 2008/030484 | 3/2008 |
| WO | WO 2009/104921 | 8/2009 |
| WO | WO 2011/004381 | 1/2011 |
| WO | WO 2012/100053 | 7/2012 |
| WO | WO 2013/011259 | 1/2013 |
| WO | WO 2013/166456 | 11/2013 |
| WO | WO 2014/008134 | 1/2014 |
| WO | WO 2014/052874 | 4/2014 |
| WO | WO 2014/100519 | 6/2014 |
| WO | PCT/US15/40228 | 7/2015 |
| WO | PCT/US15/40229 | 7/2015 |
| WO | PCT/US15/47059 | 8/2015 |
| WO | WO 2016/007969 | 1/2016 |
| WO | WO 2016/007970 | 1/2016 |
| WO | WO 2016/039991 | 3/2016 |

OTHER PUBLICATIONS

U.S. Appl. No. 14/798,049, John E. Cronin, Whistle Play Stopper, filed Jul. 13, 2015.
U.S. Appl. No. 14/798,081, John E. Cronin, Smart Field Goal Detector, filed Jul. 13, 2015.
U.S. Appl. No. 14/798,091, John E. Cronin, Real-Time Data Collection and Selective Storage, filed Jul. 13, 2015.
U.S. Appl. No. 14/798,131, John E. Cronin, Real-Time Data Collection and Storage for Use in Fantasy Football, filed Jul. 13, 2015.
U.S. Appl. No. 14/798,270, John E. Cronin, Sensor Experience Shirt, filed Jul. 13, 2015.
U.S. Appl. No. 14/798,204, John E. Cronin, Movement Monitoring Unit, filed Jul. 13, 2015.
U.S. Appl. No. 14/798,190, John E. Cronin, Player Movement Data Drives Video Game, filed Jul. 13, 2015.
U.S. Appl. No. 14/829,598, John E. Cronin, Facial Recognition for Event Venue Cameras, filed Aug. 18, 2015.
U.S. Appl. No. 14/788,728, John E. Cronin, Player Movement Data, filed Jun. 30, 2015.
U.S. Appl. No. 14/788,742, John E. Cronin, Event Video Capture, filed Jun. 30, 2015.
U.S. Appl. No. 14/798,035 Office Action mailed Nov. 24, 2015.
U.S. Appl. No. 14/798,057 Office Action mailed Nov. 24, 2015.
U.S. Appl. No. 14/798,131 Office Action mailed Jan. 12, 2016.
U.S. Appl. No. 14/798,204 Office Action mailed Jan. 22, 2016.
U.S. Appl. No. 14/798,190 Office Action mailed Jan. 12, 2016.
U.S. Appl. No. 14/829,598 Office Action mailed Feb. 2, 2016.
U.S. Appl. No. 14/788,728 Final Office Action mailed Feb. 1, 2016.
U.S. Appl. No. 14/788,742 Final Office Action mailed Jan. 6, 2016.
U.S. Appl. No. 15/187,100, John E. Cronin, Smart Field Goal Detector, filed Jun. 20, 2016.
U.S. Appl. No. 14/798,091 Office Action mailed Aug. 18, 2016.
U.S. Appl. No. 14/798,190 Final Office Action mailed Jul. 25, 2016.
U.S. Appl. No. 14/829,598 Final Office Action mailed Jul. 18, 2016.
U.S. Appl. No. 14/788,728 Office Action mailed Jul. 13, 2016.
U.S. Appl. No. 14/798,049 Final Office Action mailed Mar. 22, 2016.
U.S. Appl. No. 14/798,091 Office Action mailed Mar. 28, 2016.
U.S. Appl. No. 14/798,131 Final Office Action mailed May 23, 2016.
U.S. Appl. No. 14/798,204 Final Office Action mailed May 11, 2016.
U.S. Appl. No. 14/788,742 Office Action mailed May 11, 2016.

(56) References Cited

OTHER PUBLICATIONS

U.S. Appl. No. 14/798,131 Office Action mailed Sep. 20, 2016.
U.S. Appl. No. 15/333,711, John E. Cronin, Professional Workout Simulator, filed Oct. 25, 2016.
U.S. Appl. No. 14/788,728 Final Office Action mailed Dec. 6, 2016.
"About Head Case", Head Case Company, Sep. 24, 2013.
"Adidas' miCoach Speed_Cell and miCoach Football App Aim to Advance the Performance of Next-Generation Athletes Through New Technology", miCoach, Nov. 22, 2011.
"Advanced E-Team: Automatic Sports Time Stopping Whistle", Rose-Hulman Institute of Technology, 2002, NCIIA Funded Advanced E-Teams. Date of Download: Jun. 14, 2014. http://www.nciia.org/WebObjects/NciiaResources.woa/wa/View/GrantProfile?n=1000037.
"Affordable Concussion Management System for Young Athletes Offered by Head Case", Head Case Company, Sep. 24, 2013.
Ancona et al., N.; "Goal detection in football by using Support Vector Machines for classification" Neural Networks, vol. 1, pp. 611-616, 2001.
"AutoScout" ADSC Illinous at Singapore Pte Ltd. Sep. 21, 2015.
Belzer, Jason; "NFL Partners With Zebra Technologies to Provide Next Generation Player Tracking", Forbes/Sports Money, Jul. 31, 2014.
Brolinson et al., P. Gunner; "Analysis of Linear Head Accelerations from Collegiate Football Impacts", Current Sports Medicine Reports, 2006, vol. 5:23-28.
"Chapter 29. Outdoor Laser Operations", U.S. Department of Transportation, Feb. 9, 2012.
Cooley, Chris; "MMQB: Smart Football", The Official Blog of Chris Cooley, Jul. 13, 2009.http://chriscooley47.blogspot.com/2009/07/mmqb-smart-football.html.
"Create Innovative Services with Play Apps", Date of Download: Jan. 16, 2014, http://www.oledcomm.com/LIFI.html, Oledcomm—France LiFi.
Danakis, C et al.; "Using a CMOS Camera Sensor for Visible Light Communication"; 3rd IEEE Workshop on Optical Wireless Communications; [online], Dec. 3-7, 2012 [retrieved Aug. 14, 2015]. Retrieved from the Internet: <URL: https://195.134.65.236/IEEE_Globecom_2012/papers/p1244-danakis.pdf> pp. 1244-1248.
Dawson, Keith; "LiFi in the Real World" All LED Lighting—Illuminating the LED Community, Jul. 31, 2013.
Delgado, Rick; "Why Fantasy Football Is Embracing Big Data", Sporttechie, Jan. 3, 2014.
"Dutch Football Fans Get the Ajax Experience With AV Technology From Electrosonic", Electrosonic Press Release, May 14, 2012.
FAQ, Go Pro Workouts, Date of Download: Apr. 30, 2014 https://www.goproworkouts.com/faqs.
"First Down Laser Systems to enhance game of football and fans in-stadium experience with green line", Sports Techie, Sep. 9, 2013.
"Football Workout Programs", Go Pro Workouts. Date of Download: Apr. 27, 2014 https://www.goproworkouts.com/workouts/football.
Freeman, Mark; "Frickin' Laser Beams", River Valley Leader, Feb. 19, 2013.
Gerhardt, Ryan; "Concussion Sensing Helmet Could Save Athletes", PSFK, Oct. 28, 2013.
Gerhardt, Ryan; "Vibrating Jersey Lets Fans Feel What Players Do on the Field", PSFK.com, Mar. 13, 2014.
"GoalControl to provide goal-line system at World Cup in Brazil", BBC Sport, Apr. 2, 2013.
Gorman, Michael; "Outstanding Technology brings visible light communication to phones and tablets via dongle and LEDs", Edgadget International Editions, Jul. 16, 2012.
"Growing data sets alter Sportsvision's real-time viewing experience", Sports Illustrated, More Sports, Nov. 29, 2013.
Haas, Harald; "Delivering safe and secure wireless communications", pureLiFi. Date of download: Jan. 16, 2014 http://purelifi.co.uk/.
"How to compare personal stats with the Pros?", Support Home Discussions Training with miCoach. Jul. 4, 2012.

"How to wear the Stride Sensor (inside the shoe)", by micoach, Guides & Tutorials, May 29, 2014.
Inamoto et al., Naho; "Immersive Observation of Virtualized Soccer Match at Real Stadium Model", Proceedings of the Second IEEE and ACM International Symposium on Mixed and Augmented Reality (ISMAR '03), 2003.
"Intel, NFL Legend Jerry Rice and others Team Up to "Look Inside the Huddle" On and Off the Field", by INTELPR in Intel Newsroom, Aug. 28, 2013.
Kumar, Navin; "Visible Light Communications Systems Conception and VIDAS", IETE Technical Review, vol. 25, Issue 6, Nov.-Dec. 2008. Date of download: Nov. 19, 2009. http://www.tr.ietejournals.org.
La Confora, Jason; "NFL collecting data that could revolutionize websites, video games", CBS Sports—NFL Insider, Nov. 25, 2012.
Laviers, Kennard R.; Sukthankar, Gita; "Using Opponent Modeling to Adapt Team Play in American Football", Plan, Activity, and Recognition, Elsevier, 2014. School of ECE, Air Force Institute of Technology. Preprint submitted: Oct. 31, 2013.
LiFi Overview—Green wireless mobile communication—LiFi Technology. Date of download: Jan. 16, 2014.
Li, Yang et al., "VICO: A Framework for Configuring Indoor Visible Light Communication Networks" Aug. 11, 2012, Mobile Adhoc and Sensor Systems (MASS), 2012 IEEE 9th International Conference, Las Vegas, NV.
Macleod, Robert; "New football helmet sensors monitor brain injuries", The Globe and Mail, Nov. 14, 2013.
Madden, Lance; "Pro Athletes Share Personal Workout Secrets With Startup 'Go Pro Workouts'", Forbes.com, SportsMoney. Mar. 4, 2013.
Maricle, Charles; "Federal rules for outdoor laser user in the U.S. (FAA authority over airspace)", Laser PointerSafety.com, Apr. 23, 2014.
"Methods to Our Madness", Football Outsiders Information, Innovative Statistics, Intelligent Analysis, http://www.footballoutsiders.com/info/methods, Date of Download: Apr. 10, 2014.
Miller, Mark J.; "NFL Sensors Will Track Player Stats for Fans, but What About Safety?", Sports in the Spotlight—brandchannel, Aug. 11, 2014.
Montero, Eric, "Design and Implementation of Color-Shift Keying for Visible Light Communications", Sep. 2013, McMaster University.
Morgan, Debra; "Referee Uses Capital Idea to Stop Game Clocks on a Whistle", Loca News. Nov. 18, 1999. http://www.wral.com/news/local/story/138889.
Naidu, Vinaya; "Watched the IPL? Now Find and Tag Yourself in the Stadium With Vodafone Fancam", Business 2 Community, May 22, 2013.
"New courtside technology unveiled at PISD tourney", Precision Time Systems—New Inventions That Prevent Human Errors in Sports Timekeeping, Date of Download: Apr. 23, 2014.
Nguyen et al., "A Novel like switching scheme using pre-scanning and RSS prediction in visible light communication networks", EURASIP Journal on Wireless Communications and Networking, 2013.
"Nike+ SportBand User's Guide", by nikeplus.com, Jun. 7, 2014.
"Nokia Lumia 920 pricing compared to iPhone 5 and Samsung Galaxy SIII", by Nokia, Sep. 30, 2012.
Ogawa; "Article about VLC Guidance developed", Visible Light Communications Consortium (VLCC), Aug. 31, 2012.
Ogawa; "iPhone app from CASIO", Visible Light Communications Consortium (VLCC), Apr. 26, 2012.
Ogus, Simon; "SportIQ Announces a Game Changing Real-Time Basketball Analytics Platform", Sporttechie.com, Mar. 7, 2014.
"Omega introduces new timing equipment for ice hockey at Sochi 2014 Olympic Winter Games", OMEGA Watches, Feb. 16, 2014.
"Outdoor Laser Operations", Advisory Circular, U.S. Department of Transportation, Dec. 30, 2014.
Perin et al., Charles; "Real-Time Crowdsourcing of Detailed Soccer Data", IEEE, Oct. 2013.
Povey, Gordon, "VLC for Location, positioning and navigation", Jul. 27, 2011, http://visiblelightcomm.com/vlc-for-location-positioning-and-n . . . .

(56) References Cited

OTHER PUBLICATIONS

"Riddell InSite Impact Response System", Riddell InSite. Oct. 18, 2013.
Roble, Bob; "Inside the Huddle: How Big Data Is Unlocking Fantasy Football Insights", IQ Sports—Sports Technology, Sep. 3, 2013.
Saag, Tonis; "You can compare your training data with friends again", SportlyzerBlog, Feb. 20, 2013.
"What is SafeBrain", SafeBrain Systems Inc. May 14, 2014.
Schoonmaker, Aaron; "NCAA ignoring own clock recommendations in tourney", WRALSportsFan.com, Mar. 25, 2014 http://www.wralsportsfan.com/ncaa-ignoring-own-clock-recommendations-in-tourney/13510770/.
"Smartabase—The complete solution for athlete data management", Fusion Sport, www.fusionsport.com, Jul. 21, 2011.
"Sports Event Services—Quality Information is the first gold medal at any event", Infostrada Sports, May 24, 2013.
Stein, Anne; "Devices help alert teams to potential concussions on the field", Tribune Newspapers, Jun. 27, 2012.
Thanigavel, M.; "Li-Fi Technology in Wireless Communication", International Journal of Engineering Research & Technology (IJERT), ISSN: 2278-0181, vol. 2 Issue 10, Oct. 2013.
"The Head Case Impact Sensor", Head Case Company, Sep. 24, 2013.
"The System Models & How They Work", Precision Time Systems—New Inventions That Prevent Human Errors in Sports Timekeeping, Date of Download: Apr. 24, 2014.
"The Wearables Coaching an Optimal Version of You", by PSFK Labs, iQ, Feb. 24, 2014.
"Train like professional athletes", Go Pro Workouts. Date of Download: Apr. 30, 2014 https://www.goproworkouts.com/.
"Viewing other miCoach stats", Support Home Discussions Training with miCoach, Jun. 26, 2012.
WKO—Hunter Allen—Peaks Coaching Group Oct. 14, 2015.
"Wirless Whistle System", Bodet Sport, Sport Display—Timer. Date of Download: Jun. 23, 2014 file:///C|/king/AOP/Wireless%20Whistle%20system.htm[Jun. 23, 2014 7:32:06 PM].
Won, Eun Tae; "Visible Light Communication: Tutorial", Project: IEEE P802.15 Working Group for Wireless Personal Area Networks (WPANs), Mar. 9, 2008.
"Link: Would You Like to See the Goal-Post Lengthened in Height in College Football", TideFans.com, May 6, 2014. http://www.tidefans.com/forums/showthread.php?t=222422&page=4.
PCT Application No. PCT/US2015/033613 International Search Report and Written Opinion mailed Sep. 1, 2015.
PCT Application No. PCT/US2015/040228 International Search Report and Written Opinion mailed Sep. 30, 2015.
PCT Application No. PCT/US2015/040229 International Search Report and Written Opinion mailed Oct. 1, 2015.
PCT Application No. PCT/US2015/047059 International Search Report and Written Opinion mailed Nov. 9, 2015.
U.S. Appl. No. 14/798,049 Office Action mailed Nov. 3, 2015.
U.S. Appl. No. 14/798,081 Office Action mailed Sep. 28, 2015.
U.S. Appl. No. 14/798,091 Office Action mailed Sep. 22, 2015.
U.S. Appl. No. 14/788,728 Office Action mailed Sep. 17, 2015.
U.S. Appl. No. 14/788,742 Office Action mailed Sep. 2, 2015.
U.S. Appl. No. 15/091,139 Office Action mailed Jan. 11, 2017.
U.S. Appl. No. 14/798,204 Office Action mailed Dec. 20, 2016.
U.S. Appl. No. 14/798,131 Final Office Action dated Mar. 21, 2017.
U.S. Appl. No. 14/798,190 Office Action dated Mar. 8, 2017.

* cited by examiner

FIG. 5 — Hit History Database

| Game | Time | Sensor | Force |
|---|---|---|---|
| 5 | 0:00:50 | #3 | 15g |
| 5 | 0:05:00 | #1 | 10g |
| . | | | |
| . | | | |
| . | | | |
| 4 | 1:01:00 | #2 | 3g |
| . | | | |
| . | | | |
| . | | | |

FIG. 6 Settings Database

| Sensor ID | # | Location |
|---|---|---|
| 10996 | 1 | Head |
| 02215 | 2 | L Elbow |
| . | | |
| . | | |
| . | | |
| . | | |

FIG. 12

History Database

| | User 1 | User 2 | User 3 | User n |
|---|---|---|---|---|

| Date | Time | Game | Location | Severity |
|---|---|---|---|---|
| 4/13/2014 | 3:31 | 003 | R. Knee | 3 |
| 4/13/2014 | 3:20 | 003 | Head | 17 |
| ... | | | | |
| 4/5/2014 | 7:45 | 002 | L. Arm | 25 |
| 4/5/2014 | 7:22 | 002 | Lower Back | 9 |

FIG. 14

Thresholds Database

| User 1 | User 2 | User 3 | User n |

| Setter | Sensor ID | Location | Threshold |
|---|---|---|---|
| Dr. McCoy | 12544 | L. Arm | 75 |
| Dr. McCoy | 10966 | Head | 40 |
| ... | | | |
| Coach Zee | 24601 | L. Arm | 60 |
| Coach Zee | 10966 | Head | 30 |
| ... | | | |
| User 1 | 15478 | R. Knee | 50 |
| User 1 | 10966 | Head | 25 |

PLAYER HIT SYSTEM

CROSS-REFERENCE TO RELATED APPLICATIONS

The present application claims the priority benefit of U.S. provisional application No. 62/023,588 filed Jul. 11, 2014 and entitled "Player Hit History," U.S. provisional application No. 62/029,588 filed Jul. 28, 2014 and entitled "Hit Warning System," and U.S. provisional application No. 62/029,624 filed Jul. 28, 2014 and entitled "Player Hit Associated with Realtime Video," the disclosures of which are incorporated herein by reference.

BACKGROUND OF THE INVENTION

Field of Invention

The present invention generally relates to collecting player hit data. More specifically, the present invention relates to a player hit system.

Description of the Related Art

Wearable sensors are used nowadays to obtain a number of different types of information about the user associated with the wearable sensors. For example, some different wearable sensors may include accelerometers, gyroscopes, compasses, global positioning systems (GPS) and heart rate monitors. Through the use of these and other location-based or health-based sensors, wearable sensors can obtain a variety of different information about the particular user associated with the wearable sensors.

Use of the wearable sensors can be incorporated, for example, in obtaining information about various physical contact experienced by a player in a contact sport (e.g., football). Factors such as hit intensity type, direction of the hit, and location of where the hit was experienced can be calculated based on the use of one or more sensors associated with the user. The information obtained from the sensors can be processed and outputted onto graphs for viewing.

Contact sports, such as football, can be taxing on the body of the player. Currently there is no available way for a user to measure and evaluate the impact of various different physical contacts (i.e. hits) experienced by a player over a period of time. There is also no easy way for a user to view the information (e.g., in-game video recordings) pertaining to the physical contacts. It should be noted that the cumulative effects of experiencing repeated hits may not be easily measurable, quantifiable or identifiable. For example, pains experienced by the user (e.g., back pains, neck pains) may be tough for a player to quantify over a long period of time. Figuring out what types of physical contact caused what body pains may be difficult. It may also be difficult to accurately quantify the seriousness of physical contact between past experiences and physical contact that the player may currently be experiencing in-game.

There is also a need to provide warnings to coaches, players and medical officials regarding impending injuries that may surface based on the various physical contacts experienced by the player. In particular, once a threshold of pain is experienced by a player, a warning should be provided to inform coaches, players and medical professionals about impending injuries that players may experience from continued physical contact.

SUMMARY OF THE CLAIMED INVENTION

A method for monitoring physical contact within a game is claimed. The method first obtains setting information for monitoring the physical contact within a game (e.g., American football) associated to one or more players participating within the game. The method collects sensor data for each of the players based on the settings information. The sensor data is then evaluated to separate sensor data corresponding to detected physical contact (e.g., tackle) from sensor data not related to physical contact (e.g., movement). The detected physical contact information can then be processed and displayed on a graphical user interface for users (e.g., players, coaches, medical professionals) to view.

A system for monitoring physical contact within a game is also claimed. The system includes a user interface and a processor. The processor executes instructions stored in memory to obtain setting information for monitoring the physical contact within a game (e.g., American football) associated to one or more players participating within the game. The system collects sensor data for each of the players based on the settings information. The sensor data is then evaluated to separate sensor data corresponding to detected physical contact (e.g., tackle) from sensor data not related to physical contact (e.g., movement). The detected physical contact information can then be processed and displayed on a graphical user interface for users (e.g., players, coaches, medical professionals) to view.

BRIEF DESCRIPTION OF THE DRAWINGS

FIG. 5 illustrates the hit database.

FIG. 6 illustrates the settings database.

FIGS. 12-14 illustrate exemplary databases for use with the player hit system.

DETAILED DESCRIPTION

The systems and methods described herein are directed towards collecting and recording data pertaining to physical contact experienced by players in a contact sport (e.g., football). The data can be collected and recorded through the use of one or more sensors worn by the player. In some cases, the sensor data can be associated with in-game video recordings of physical contact experienced by the players.

The systems and methods can then evaluate the collected data and provide information to the player, coaches or medical professionals (e.g., doctors, physical therapists) summarizing the physical contact experienced by the players. The information can be display on a graphical user interface (GUI) for the player, coaches or medical professionals to view. In some cases, the information may be used as part of a warning system to notify of potential injuries that may arise from experiencing continued physical contact.

It should be noted that the embodiments described herein when describing the present invention are directed towards the sport of American football. The embodiments, however, are not solely limited to American football. Other sports, such as soccer and hockey may also utilize the present invention in order to monitor physical contact experienced within a game and provide information about potential injuries resulting from the physical contact.

Figure 1:
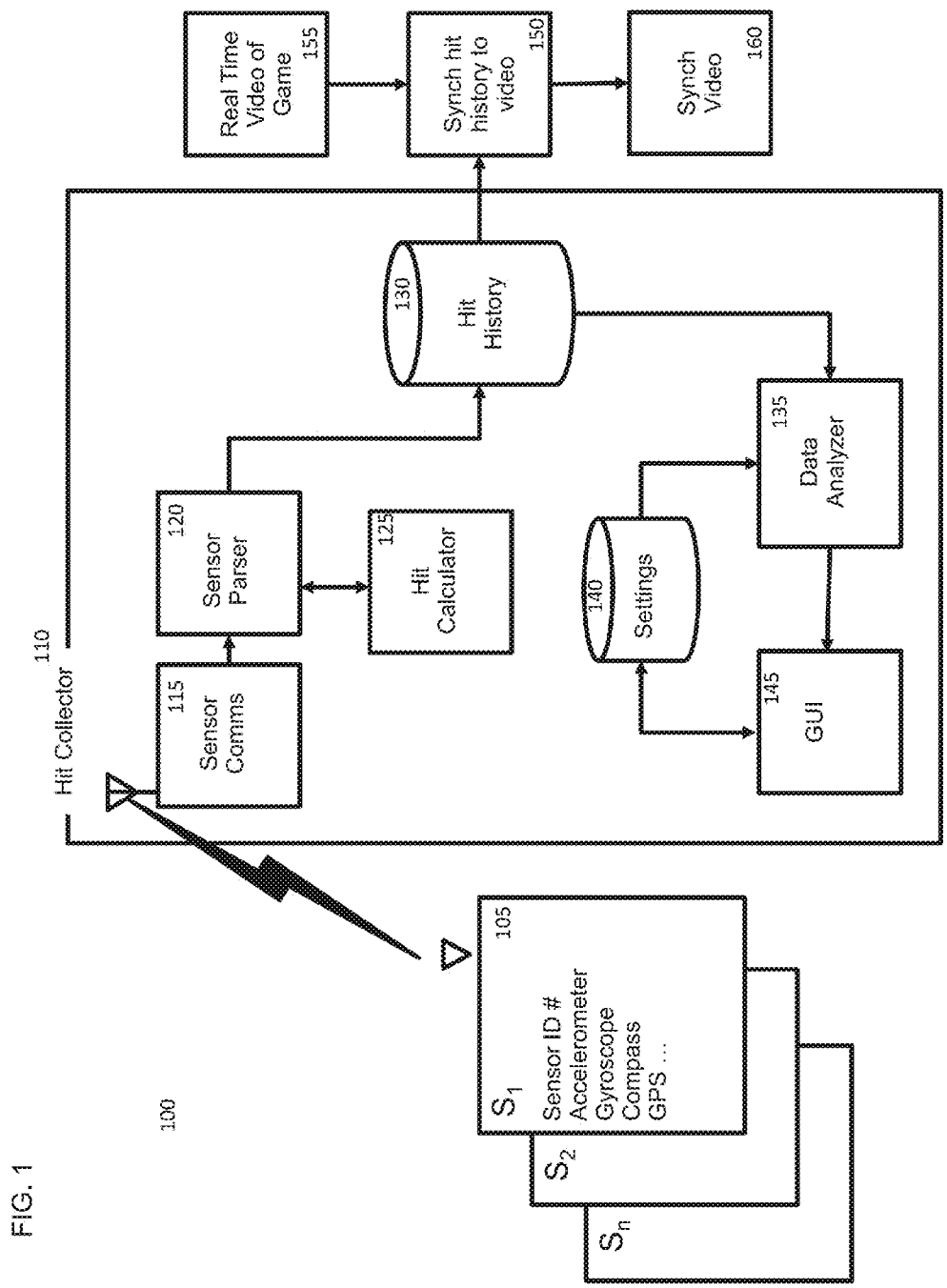
FIG. 1 illustrates one embodiment of the player hit system 100.

FIG. 1 illustrates one embodiment of the player hit system 100. The player hit system 100 is directed at collecting, recording, evaluating and outputting information pertaining to physical contact (i.e. player hits) experienced by a player.

The player hit system 100 includes a number of different elements described in detail herein. First of all, the player hit system 100 may include one or more sensors 105 that are used to collect data about physical contacts experienced by a player. For example, such data may include where a football player experienced a tackle from one or more opposing football players during a football game.

The sensors 105 used to collect the data may include various types of sensors currently available including accelerometers, gyroscope, compass, and GPS. It should be noted that other location-based, motion-based or health-based sensors may also be used to record data about the player related to physical contact. These sensors 105 can be used to monitor, for example, movement by the player but also capture sudden movements and other reactions by the player that may correspond with in-game physical contact (e.g., a tackle). The sensors 105 may be associated with the player being monitored by being embedded in the uniform worn by the player. In some embodiments, there may be sensors physically affixed to the body of the player.

Each of the sensors 105 can provide sensor data obtained to the hit collector system 110 via the sensor communication module 115 of the hit collector 110. The communication between the sensors 105 and the hit collector system 110 may be wireless. The hit collector system 110 is used to collect all sensor data from the various sensors 105 associated with a player and subsequently process the sensor data to provide information about the physical contact. The sensors 105 may each have a unique sensor identification that can be transmitted alongside the sensor data. The unique sensor identification may be used so that the data may be organized and stored by the hit collector system 110, for example, based on a particular player or by data type.

The sensor data from the sensors 105, obtained by the sensor communication module 115, are transmitted to the sensor parser 120. The sensor parser formats the sensor data so that the hit calculator 125 can properly process the sensor data. In particular the hit calculator 125 can differentiate sensor data corresponding to physical contact (i.e. hits) from sensor data corresponding to merely movement or other non-physical contact related data. In some embodiments, information about the physical contact may also be extracted from the sensor data including the location and intensity of the physical contact. Further details on how the hit collector system 110 determines what sensor data corresponds to physical contact is provided below (e.g., FIG. 2).

The data corresponding to physical contact can then be stored by the hit collector system 110 into a hit database 130 for future reference. The remaining data may be ignored or disregarded.

The hit collector system 110 may also include a GUI 145 from which users (e.g., coaches, players, medical professionals) of the hit collector system 110 may view the sensor data obtained by the sensors 105. The data analyzer 135 retrieves stored sensor data pertaining to physical contact from the hit database 130. The type of data obtained may be dictated by one or more settings 140, which may be customized by the users.

Even though the information displayed on the GUI 145 may be helpful in detailing the physical contact experienced by a player during a game, it may be beneficial to also include video recordings of the physical contact alongside the data as well. The video recordings may provide another way of detailing the intensity and severity of physical contact that may not be possible solely through the use of the sensors 105.

To facilitate use of the video recordings of the physical contact experienced by a player, the hit collector system 110 may also include real time video of the game 155 from which the player is participating in. The sensor data obtained from the sensors 105 and subsequently stored in the hit database 130 can be synchronized with the real time video of the game 155. Generally the sensor data will be synchronized based on time. In this way, sensor data corresponding to a physical contact can be referenced alongside a video recording of the same physical contact from the game 155. Both sets of information can be associated together via the synch video module 160.

Figure 2:
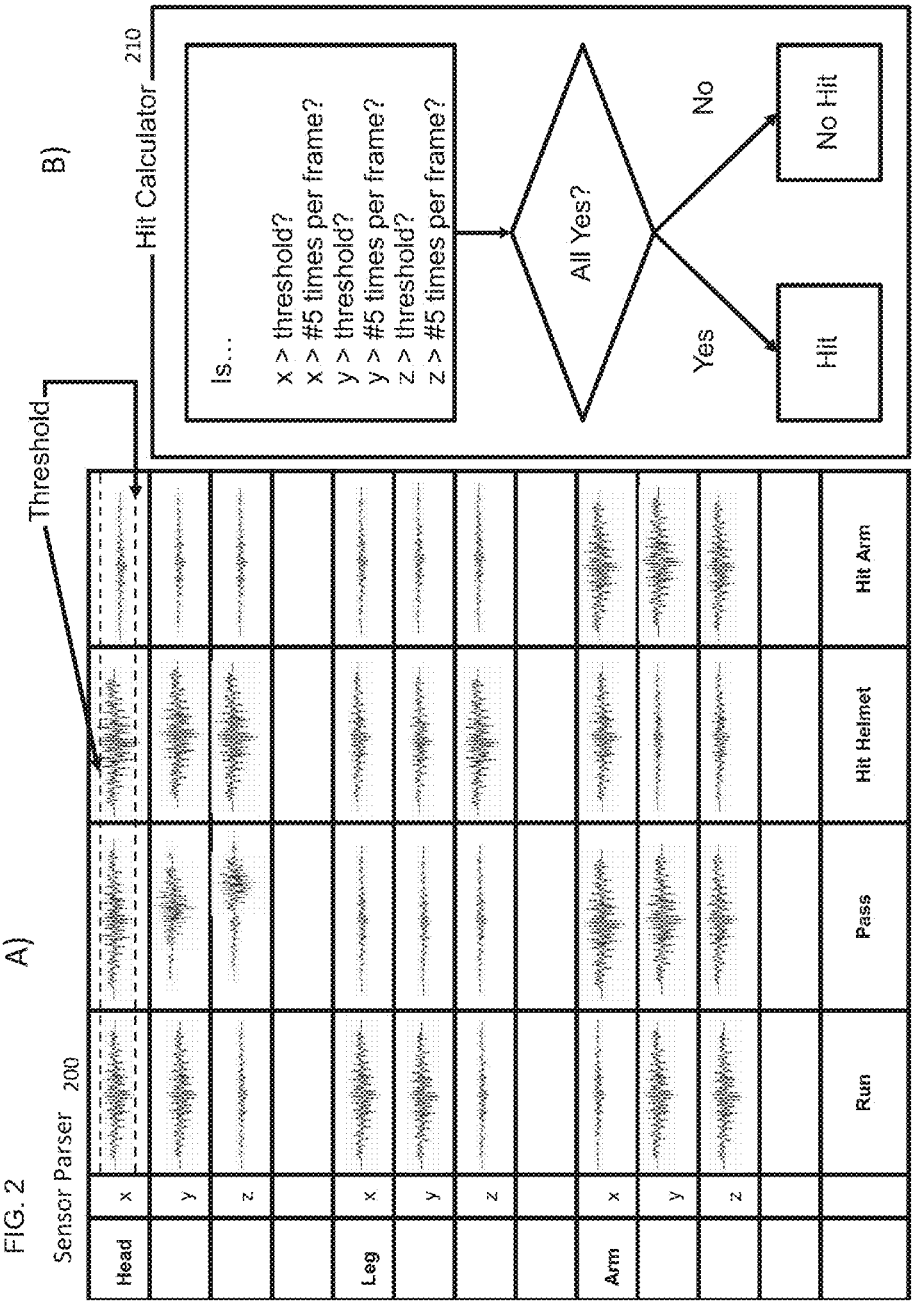
FIG. 2 illustrates an implementation of the sensor parser and the hit calculator.

FIG. 2 illustrates an implementation of the sensor parser 200 and the hit calculator 210. As described above in FIG. 1, the sensor parser 200 is used to format the sensor data being obtained by one or more sensors associated with a player. The sensor data may include location-based, health-based and motion-based data. The sensor parser 200 formats the sensor data in a way that allows the hit calculator 210 to differentiate sensor data regarding physical contact from other sensor data that does not relate to physical contact (e.g., motion-based data, health-based data).

In an embodiment, the sensor parser 200 formats data from three sensors (e.g., x, y and z accelerometers), which obtains sensor data for physical contact of a player from three bodily regions of the player (e.g., head, leg and arms). The sensor data can be organized by time periods (e.g., frames). Within each frame, the sensor data (e.g., accelerometer data) can be displayed. At least with reference to FIG. 2, the waves within the frames may be representative of motion-based data (e.g., movement from the player or physical impact from other players) obtained from the accelerometers.

The sensor data, as illustrated in FIG. 2A, may be identified for various situations. For example, the motion-based data obtained by the accelerometer may correspond with the player running, passing, being hit by another player via their helmet (e.g., tackle) or being hit by another player via their arms. Depending on the action and where the sensor data is being obtained from, the sensor data being evaluated can vary from having little to no peaks (e.g., x, y, z accelerometer data in the legs during a pass) to detecting large peaks (e.g., x, y, z, accelerometer data in the head during a helmet hit).

In situations where the sensors are obtaining sensor data for situations not involving physical contact, the sensor data displayed in FIG. 2 may correspond with little to no peaks (e.g., legs during a pass). When certain body parts are used for an activity (e.g., legs during running or arms during passing), sensor data may include more significant peaks. In any case, these sensor data may correspond for situations where no physical contact is generally involved.

The general characteristics of these activities may be usable by the hit calculator 210 to determine whether or not differences in the data obtained can indicate whether physical contact has been experienced. These general situations (obtained through one or more past sensor data cycles) may provide a comparative threshold value that can be evaluated by the hit calculator 210 for determining if physical contact is present in situation where recent sensor data obtained for the same activity is different. For example, if the sensor data exceeds the comparative threshold value, the hit calculator 210 may be capable of confirming that physical contact was experienced. If the sensor data is within the comparative threshold value, the hit calculator 210 may determine that nothing out of the ordinary has occurred.

FIG. 2B illustrates an exemplary algorithm for the hit calculator 210 for evaluating sensor data from the sensor parser 210 to determine if physical contact is present. The algorithm evaluates the sensor data for each of the sensors to determine if the sensor data is greater than a pre-defined threshold. As indicated above, the pre-defined threshold may be based on previous sensor data obtained or may be inputted, for example, based on medical studies. The algorithm also may evaluate whether the sensor data is greater than a multiple of that pre-defined threshold (e.g., five times). Based on the output regarding the evaluation of each of the sensor data, a determination can be reached by the hit calculator 210 if physical contact (i.e. a hit) has been detected.

Figure 3:
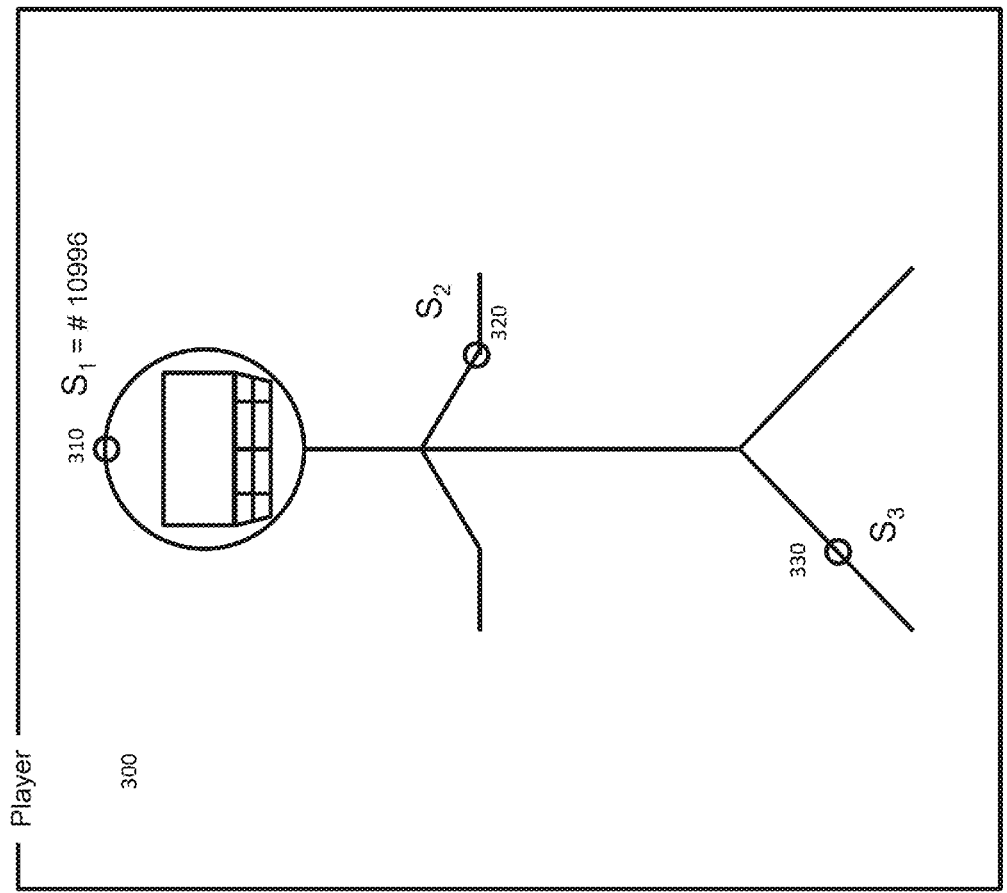
FIG. 3 illustrates a player having three sensors.

FIG. 3 illustrates a player 300 having three sensors 310, 320, 330. In an embodiment, the player 300 may have three sensors 310, 320, 330 for obtaining movement-based data during a game. These sensors 310, 320, 330 may have been used, for example, to obtain the information illustrated in FIG. 2.

As illustrated in FIG. 3, the player may have one sensor embedded in their helmet 310. Other sensors may be affixed to the uniform or directly onto the body of the player around the elbow 320 and the knee 330 of the player. It should be noted that more than three sensors can be worn on the body of the player at any time. Also, other types of sensors besides accelerometer (i.e. motion-based sensors) can also be used.

Each of the sensors 310, 320 and 330 may also have unique sensor identification (e.g., ID No. 10996). The sensor identification can be used, for example, can be used to identify in a common database which sensor data belongs to which player. The sensor identification for each respective sensor used by a player can also be displayed in the GUI along with where the sensor is located on the body of the player.

Figure 4:
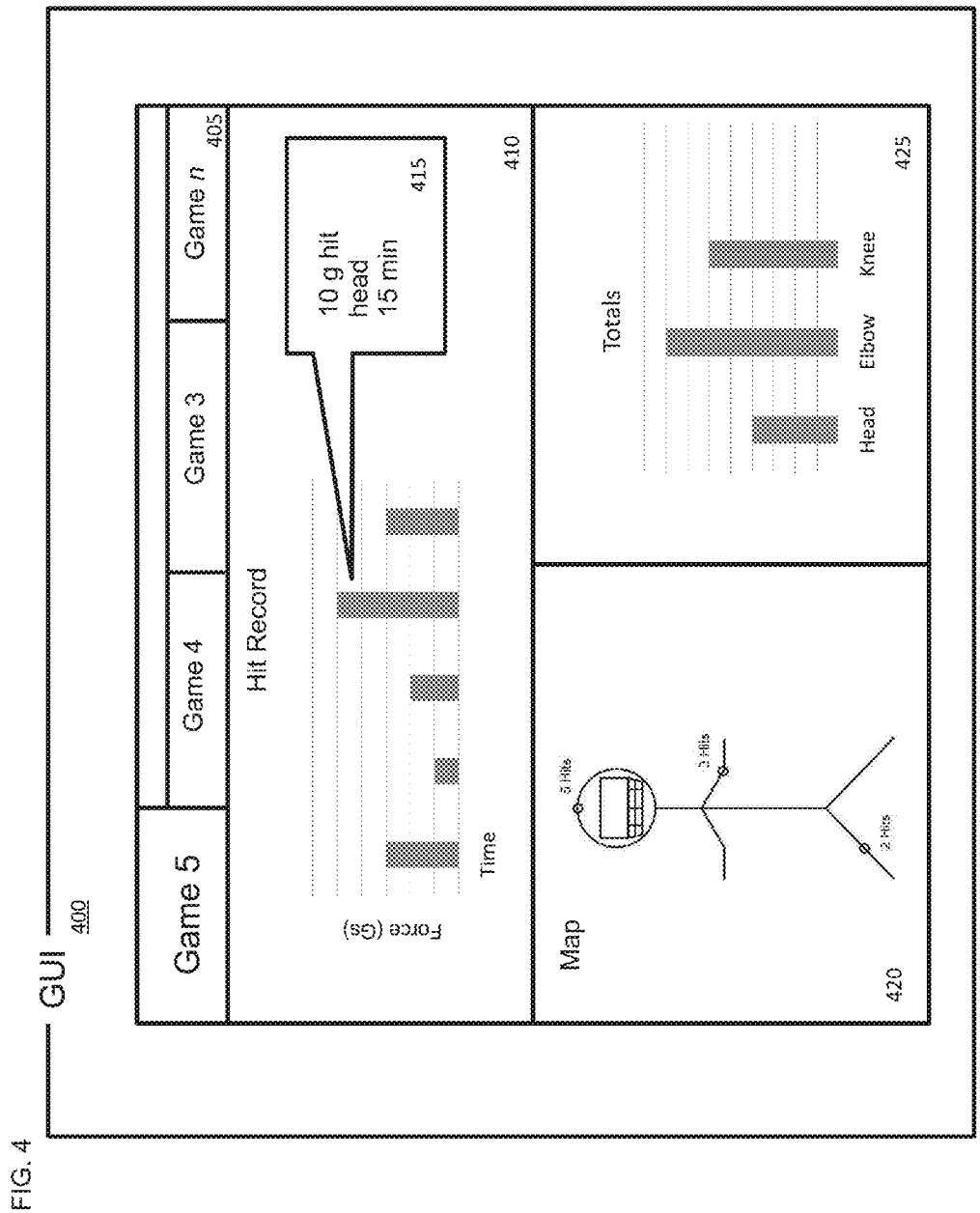
FIG. 4 illustrates a graphical user interface (GUI) for displaying physical contact experienced by a player.

FIG. 4 illustrates a graphical user interface (GUI) for displaying physical contact experienced by a player 400. More specifically, the graphical user interface displays sensor data quantifying physical contact experienced by the player.

With reference to the figure, sensor data for one or more games can be selected by the user via tabs 405 along the top of the GUI 400. For example, 'Game 5' my correspond to the most recent sensor data obtained from a player participating in a game. Tabs for Games 4, 3 and n may correspond to past games where sensor data for the player was also obtained while the player was participating in the game. The sensor data may be stored in the player hit system and recalled for viewing by selection of one or more of the tabs.

The GUI 400 also includes a hit record 410. The hit record 410 is a graph that shows a running tally of physical contact that occurred within the game. The x-axis corresponds to the time within the game and the y-axis corresponds to the force of the physical contact. An example 415 is illustrated also in FIG. 4 where information about a physical contact at the 15 minute mark was recorded. Users may request additional information by interacting with the hit record 410 in the GUI 400 (e.g., selecting one or more bars on the hit record 410 representative of a measured physical contact). Exemplary information may include the measured force of the physical contact, the location of the physical contact and the time when the physical contact was measured.

The GUI 400 may also include a map 420. The map 420 includes a tally of all the physical contacts detected on the body of the player and associates it with a particular. As illustrated in FIG. 4, the sensors on the player may have detected five hits to the head area, three hits to the arm area and two hits to the leg area. It may be possible that some physical contact can trigger multiple sensors therefore having a single physical contact count multiple times.

Lastly, the GUI 400 may include another graph 425 that is used to illustrate a total number of hits corresponding to the map 420. The total illustrated in the totals graph 425 may be directed towards a total number of hits throughout the game. In some embodiments, the totals graph 425 may also be directed towards quantifying a total amount of force experienced by the player at each respective body part. As illustrated in FIG. 4, the player may have experienced the most force in their arms so far in the game while the legs and the head has experienced less force from physical contact.

It should be noted that the different information provided in the GUI 400 are directed at providing insight to users (e.g., the players, coaches, medical professionals) regarding the physical contact experienced by the player within the game. To this end, it may be possible and within the teaching of the present invention that the GUI 400 includes different or additional information compared to what is illustrated in FIG. 4 and described herein.

FIG. 5 illustrates the hit database. The hit database (also referred to as the hit history database) stores the physical contact information obtained from the sensors associated with the player.

As illustrated in the figure, the hit database may be organized via a table having a number of columns used to characterize the data in a more ordered manner. Some exemplary columns may include identifying what game the physical contact was detected in, the time when the physical contact was detected, which sensor detected the physical contact and the severity or force of the detected physical contact.

For example, we can see from the table illustrated in FIG. 5 that the player experienced one occurrence of physical contact during game 5. The physical contact occurred 50 seconds from the start of the game. The physical contact experienced by the player was detected from sensor #3 and was measured with a force of 15 g. It should be noted that additional information may be included in the hit database that can also be used to quantify each physical contact including what areas of the body of the player the physical contact affected and a running total of the number of hits and/or force a particular body part of the player has experienced so far within the same game.

FIG. 6 illustrates the settings database. The settings database includes information taken from the GUI and the user. For example, the settings database may store each of the sensors associated with a player for monitoring physical contact. The settings database may also include corresponding sensor identification for each of the sensors associated with the player. The location for each of the sensors may also be stored in the settings database (e.g., head, arms, leg).

Figure 7:
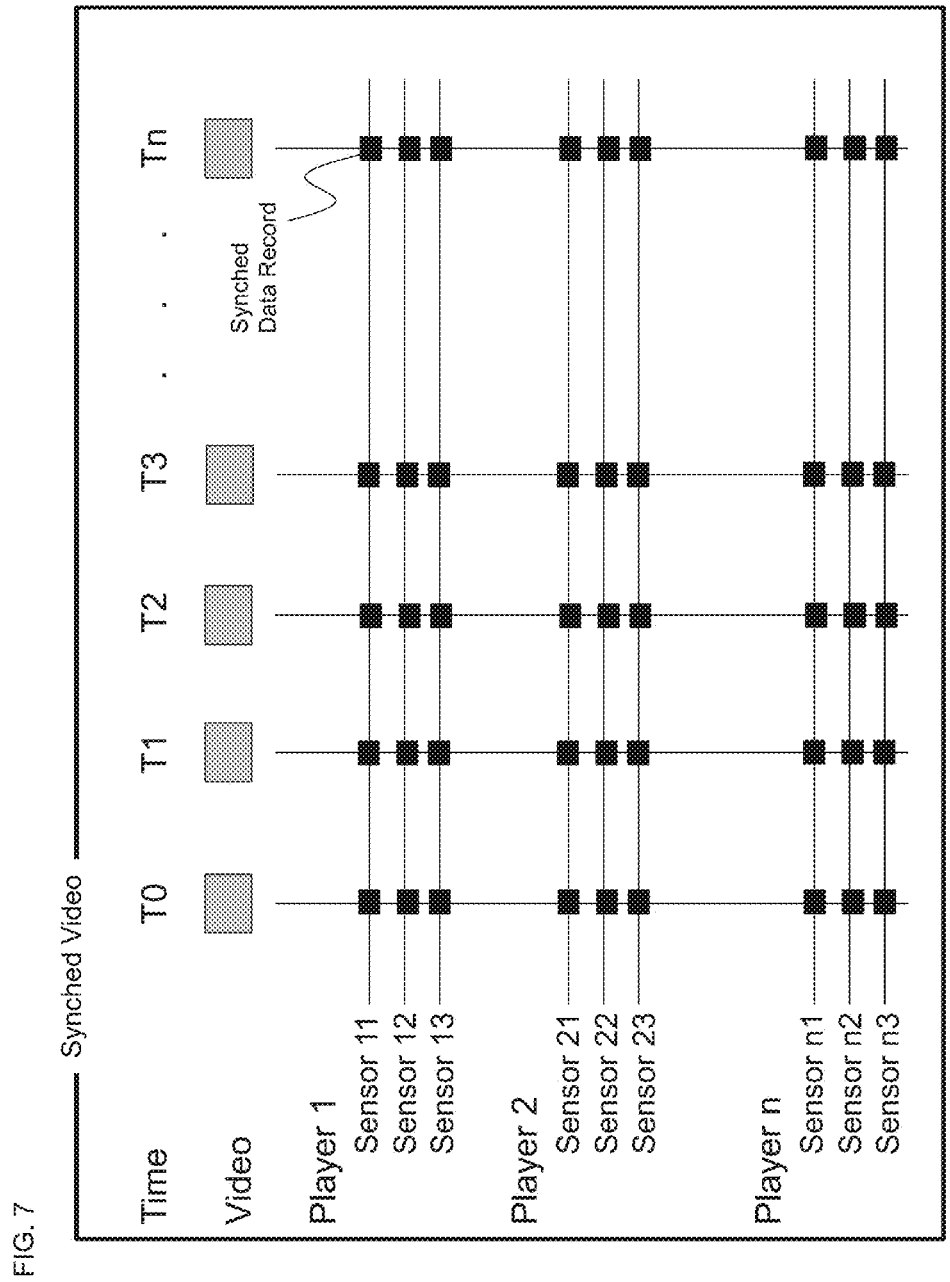
FIG. 7 illustrates the synching of the video with the hit database.

FIG. 7 illustrates the synching of the video with the hit database. In particular, the figure illustrates the videos at different time periods (e.g., T0, T1, T2, T3, Tn) along the top. Associated with each of the time periods associated with the video are sensor data stored in the hit database. The data from the hit database may include data from one or more players (e.g., player 1, player 2, player n). In this way, sensor data for physical contact of multiple players can be tied to the same in-game video.

Each of the players may use one or more sensors directed at obtaining sensor data for detecting physical contact. As illustrated in the figure, each sensor may be distinct (e.g., sensor 11, 12, 13, 21, 22, 23, n1, n2, n3) and therefore have a corresponding unique sensor identification.

Figure 8:
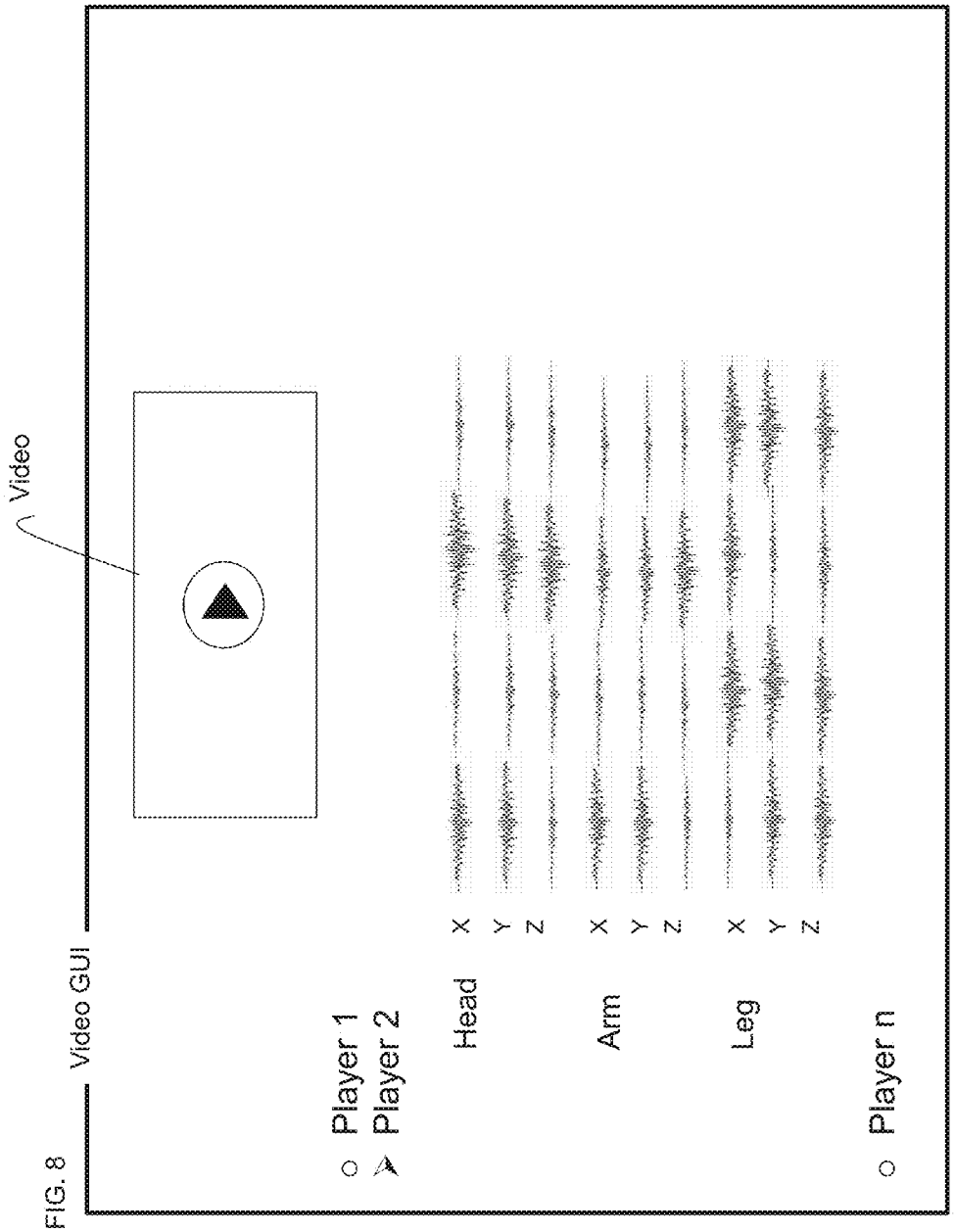
FIG. 8 illustrates the video GUI.

FIG. 8 illustrates the video GUI. The video GUI allows users (e.g., players, coaches, medical professionals) to view recorded in-game video corresponding to a corresponding sensor data related to a physical contact experienced by a player. The user can have the ability to select from one or more players that the player hit system may be monitoring.

In the video GUI, sensor data associated with the various sensors associated with the selected data may be displayed. If the sensor data is directed to physical contact that the user would like further information about from a video, the user would be capable of viewing the video that corresponds with the selected sensor data. The video that is provided has been synched with the sensor data and the user can enable options (e.g., play) to view the video.

Detecting and recording of physical contact experienced by a player within a game can be helpful. It is known that contact sports can be taxing on the body of the player. By using the sensor data regarding physical contacts, the player hit system can also provide information about possible injuries caused by continued physical contact. In this way, a warning can be provided to prevent a particular player from experiencing further physical contact near a threshold amount that may be indicative of a possible physical injury.

Figure 9:
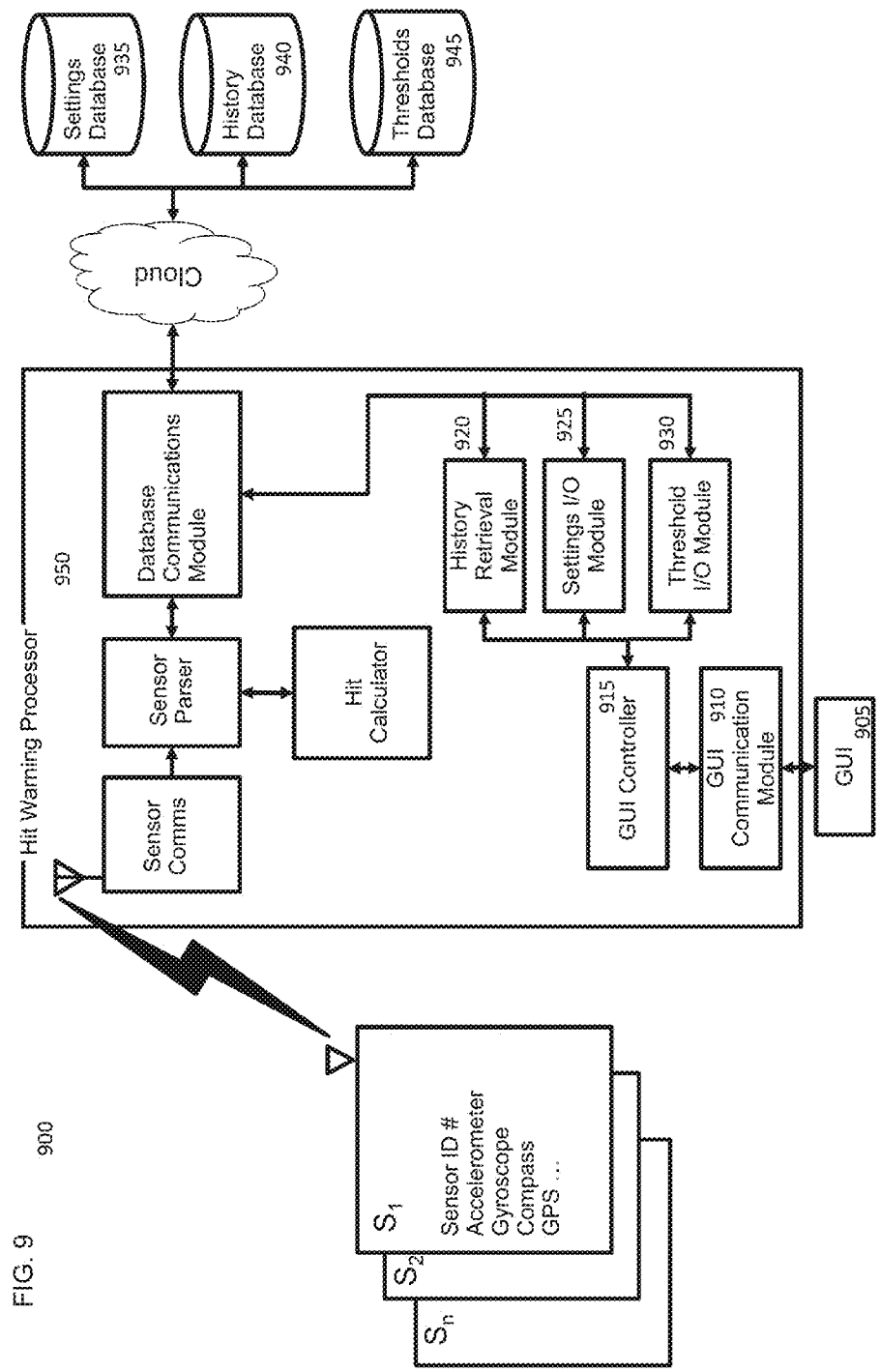
FIG. 9 illustrates a player hit system 900 directed at providing warnings.

FIG. 9 illustrates a player hit system 900 directed at providing warnings. The warnings are directed at notifying players, coaches and medical professionals that impending injury may be experienced if the player continues to experience physical contact beyond an acceptable threshold amount. Generally, the player hit system 900 can monitor and track the physical contact experienced by a player and provide warnings once the total number of occurrences of physical contact or force associated with the physical contact reaches a threshold value.

It should be noted that the player hit system 900 of FIG. 9 may be similar to the player hit system illustrated in FIG. 1. A difference may be directed at the player hit system 900 of FIG. 9 providing warnings about continued physical contact experienced by a player. There may be embodiments, however, that the player hit systems of FIG. 1 and FIG. 9 are combinable into a single player hit system capable of performing features of both player hit systems.

The player hit system 900 of FIG. 9 includes a hit warning processor 950 that receives sensor data from one or more sensors in a similar manner as the hit collector of FIG. 1. The hit warning processor 950, however, utilizes a GUI 905 that displays information (e.g., warnings) about physical contact to users (e.g., players, coaches, medical professionals). The GUI 905 receives the information via the GUI communication module 910.

The information provided to the communication module 910 is first obtained via the GUI controller 915. The GUI controller 915 obtains information regarding related thresholds, settings and physical contact that will be used by the hit warning processor 950 for one or more players being monitored by the hit warning processor 950.

The history data about past physical contact for a particular player may be obtained for the GUI controller 915 via the history retrieval module 920. The history data includes previously obtained and stored data regarding physical contact experienced by one or more players within a game. The history retrieval module 920 may obtain the information from the history database 940 that may be associated with the player hit system 900.

Similarly, the settings I/O module 925 and the threshold I/O module 930 can obtain for the GUI controller 915 the settings information from the settings database 935 and the threshold information from the threshold database 945, respectively. The settings information includes information about the identification of the sensors associated with a particular player. The settings information may also include the location of where the sensors are associated (e.g., head, arms, leg). With respect to the threshold information, this information can be provided by the users (e.g., players, coaches, medical professionals) as an indicator to what extent a player may experience physical contact without suffering an injury. The threshold information may be provided as a total number of this that a player may be able to experience. In some embodiments, these hits may be directed towards particular areas of the body of the player. The threshold may also be provided as a total amount of force that the body of the player may be capable of withstanding. Generally, the threshold dictates that further physical contact may strain and potentially cause injury to the body of the player. A warning can be provided when the amount of physical contact experienced by a player is near or exceeds the identified threshold so that the player and/or coach can take action to reduce further physical contact (e.g., refraining from further playing in the game/player substitution).

Although the settings database 935, history database 940, and the thresholds database 945 are illustrated as being databases separate from the hit warning processor 950 (i.e. the information is obtained through communicating via the cloud or Internet), there may be embodiments where the settings database 935, history database 940 and the thresholds database 945 are stored within memory associated with the hit warning processor 950.

Figure 10:
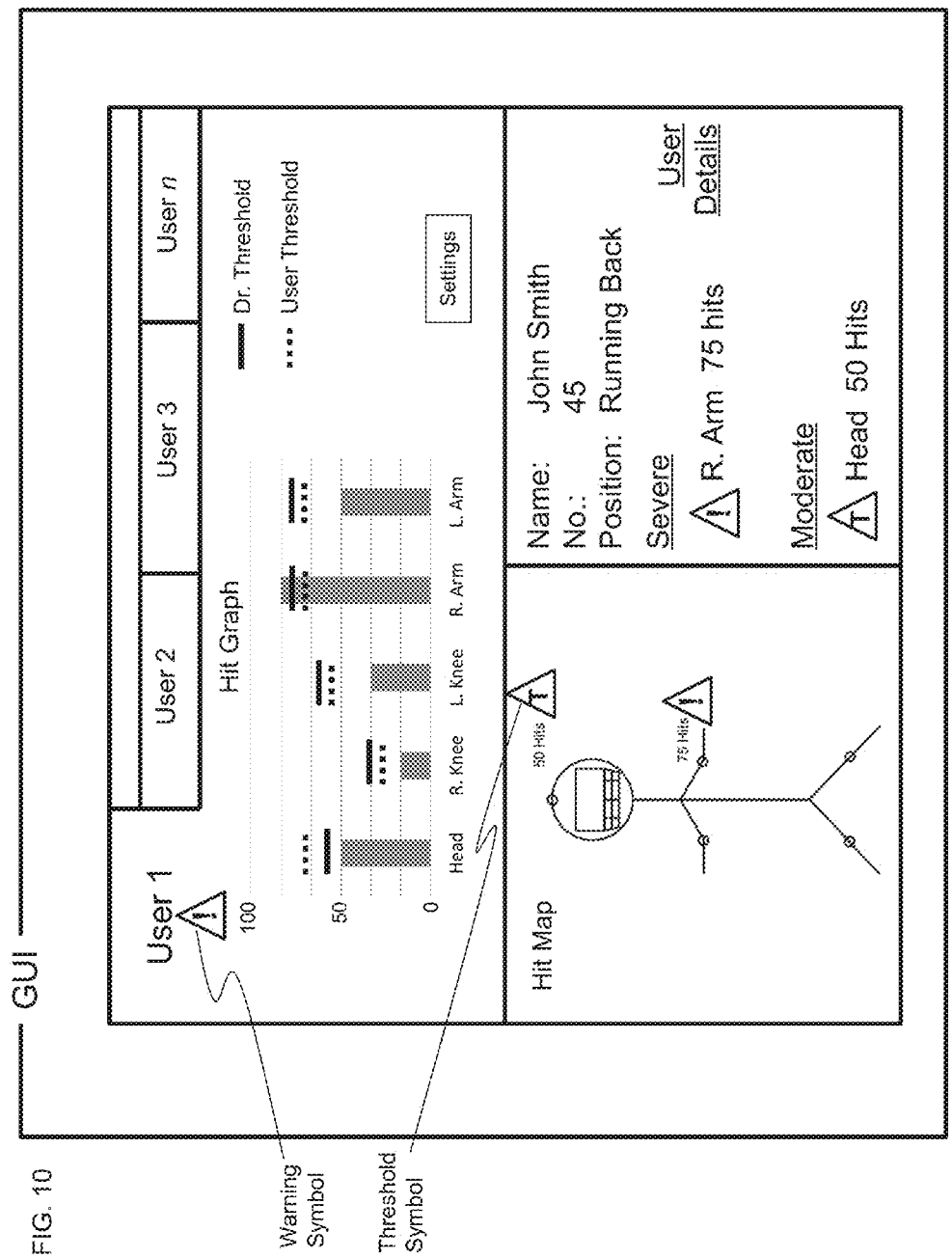
FIG. 10 illustrates a GUI for providing warnings based on experienced physical contact.

FIG. 10 illustrates a GUI for providing warnings based on experienced physical contact. The GUI illustrated in FIG. 10 may be similar to the GUI described above with respect to FIG. 4. A difference between the two embodiments, however, is directed towards the information pertaining to warnings for experienced physical contact by the user. Although the embodiments illustrated in FIG. 4 and FIG. 10 are separate, it is possible that the features of each of the GUI are combinable into a single GUI.

With the GUI illustrated in FIG. 10, a user (e.g., a player, coach, medical professional) may be capable of selecting from multiple different users (i.e. players) being monitored by the player hit system. The GUI would display the hit graph, which illustrates experienced physical contact by the particular player, and the hit map, which illustrates totals of physical contact experienced by the particular player characterized by, for example, areas where the physical contact was experienced (e.g., head, arms, leg).

In situations where a warning should be provided to a player, the user may be provided a warning symbol that is viewable on the GUI associated with the information for that particular player. The information indicated in the hit graph and the hit map may also provide an indication as to why the warning symbol is being provided. For example, with respect to the hit graph illustrated in FIG. 10, thresholds can be provided (from the user/player and medical professionals) indicating what amount of physical contact would be acceptable. In situations where the total amount of physical contact exceeded one or both thresholds, the warning symbol may be provided. It should be noted that the thresholds indicated in the hit graph may be modified via the settings and can vary based on each player being monitored by the player hit system.

Information about why the warning symbol is provided may also be provided via the hit map included in the GUI. There may be an associated number of occurrences of a physical contact that a player may experience within a period of time. If the total number of occurrences meets or exceeds the threshold allowable, this may also be indicative of a warning. The GUI may also provide a corresponding threshold symbol that can be used to inform the user that a threshold value associated with the number of hits has been met or exceeded.

With reference to the GUI, information about the player may also be provided. As illustrated in the lower right side of the GUI of FIG. 10, information about the player (e.g., name, player number and position) may be provided so that the user (e.g., coach, medical professional) can confirm with whom the data is associated. Further classification can also be provided as to what aspects of the physical contacts may pose to be a possible issue with the particular player. For example, the GUI may indicate that the number of occurrences of physical contact for the arm and head meets or exceeds allowable threshold levels. Depending on how many hits have been received based on the threshold, the classification can indicate a severity. The more severe a classification can be indicative of a greater possibility of physical injury.

Figure 11:
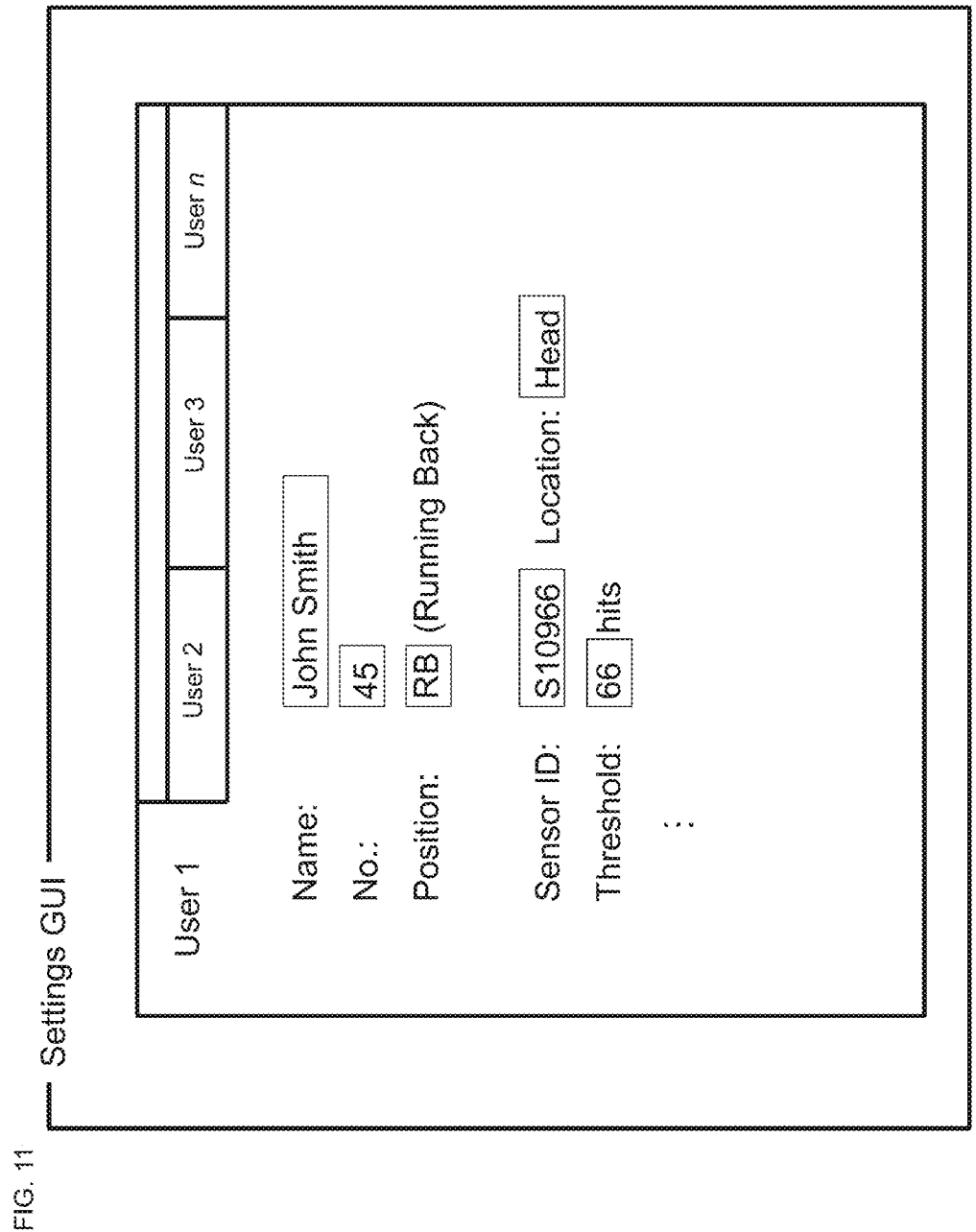
FIG. 11 illustrates the settings GUI.

FIG. 11 illustrates the settings GUI. More specifically, the settings GUI, as alluded to in FIG. 10, can be provided to allow users (e.g., players, coaches, medical professionals) to input threshold limits related to the physical contact that a player can experience within a period of time (e.g., within a game) before a warning is provided. The threshold limits may pertain to an allowed number of occurrences of physical contact within the game. The threshold limit may also pertain to a total amount of force that the player can experience within the game from the physical contact.

The settings GUI may also provide input for other types of information including user information (e.g., information about the player such as name, number and position). In this way, sensor data obtained and displayed can be readily identified and associated with a particular player.

Lastly, the settings GUI may also include the ability for the user to associate one or more sensors (via unique sensor identifications) to various portions of the body of the player. With each sensor, a threshold can also be assigned. The threshold may be associated with a total number of detected physical contacts or a total amount of force experienced. Upon experiencing a total number of hits or amount of force that meets or exceeds the threshold associated with the particular sensor, a warning can be provided to the GUI associated with the particular user.

Figure 13:
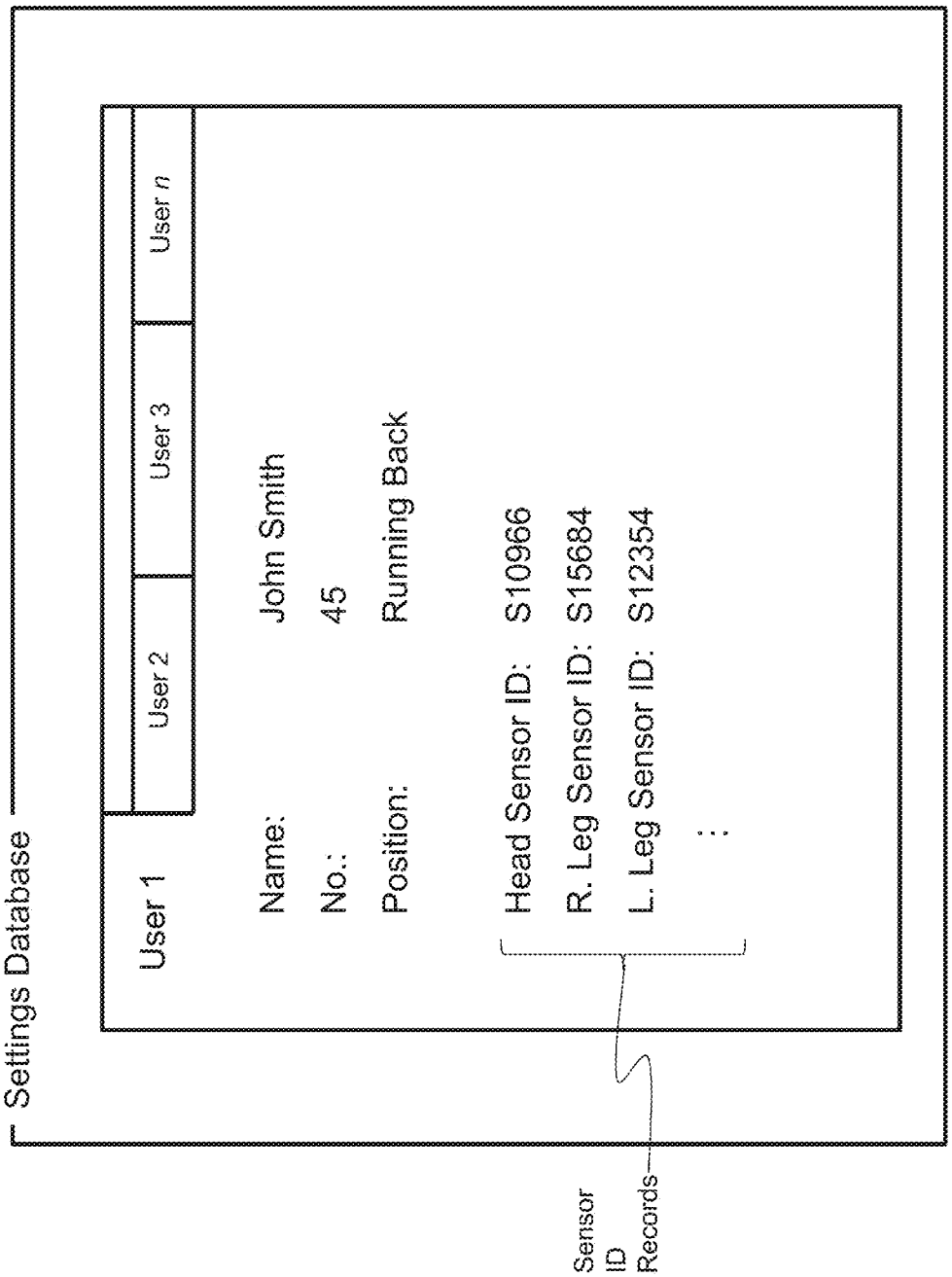

FIGS. 12-14 illustrate exemplary databases for use with the player hit system. FIG. 12 corresponds to the history database, FIG. 13 corresponds to the settings database and FIG. 14 corresponds to the threshold database. These databases may be associated with the player hit system (see, e.g., FIG. 9). Information from these databases may be stored in the cloud or in the Internet. In some embodiments, these databases may be part of memory associated with the player hit system.

With reference to FIG. 12, the history database may be similar to the hit database illustrated in FIG. 5. The history database may include information pertaining to each occurrence of a physical contact experienced by a user. The information may include when (e.g., date, time, game #) the physical contact was experienced, and where the physical contact was experienced (e.g., head, arms, leg). The history database may also include information about the severity of the physical contact. The severity may be associated with the amount of force that was measured with that particular physical contact. The severity may also be influenced by the past physical contact experienced by the player. For example, if a player continually experiences hits in the arm, continued and repeated experiences of physical contact to the arm (although may be minor) may contribute to the player experiencing a total number of hits or total amount of force that exceeds a pre-defined threshold. The severity may be indicative of the impending threshold that will be met with each subsequent experience of physical contact within the same area.

It should be noted that other types of information may also be stored in the history database illustrated in FIG. 12. For example, a total amount of force may also be recorded and stored for reference.

The history database may include information for a plurality of different users (i.e. players) being monitored simultaneously within the same game. Viewing different information may be possible through the use of the tabs (e.g., user 1, user 2, user 3, user n).

With reference to FIG. 13, information provided from the settings GUI may be stored in the settings database. This information may include personal information about the player and the sensors used by the player.

Each of the information stored in the settings database may correspond to a particular player and can be selected via the use of tabs (e.g., User 1, User 2, User 3, User n). It should be noted that the settings database may also include additional information obtained in other ways aside from the settings GUI. Such information may still be stored in the settings GUI if such information is to be associated with a particular player. For example, medical history about a particular player may be important enough to keep stored and retrieved for future reference. This information may be stored with the associated player in the settings database.

With reference to FIG. 14, information about thresholds for a particular player can be stored in the threshold database. Threshold information for each player may be organized separately. Selection of a particular player via tabs (e.g., User 1, User 2, User 3, User n) can show all the threshold-related information for that particular player.

The threshold information stored in the threshold database can include the sensor identification (i.e. unique sensor ID), location of where the sensor is associated with (e.g., head, arms, legs) and a threshold used to trigger a warning. As indicated above, the threshold may correspond to a total number of occurrences of physical contact detected by that sensor. It may also be possible to have the threshold correspond to a total amount of force experienced by that particular sensor. Also included in the threshold database may be an indicator about who inputted the threshold information (e.g., the player, coach, medical professional). These thresholds provided by different users may be the same or different. For example a player may know from experience how much physical contact he would be capable of experiencing whereas a doctor may provide a different threshold based on tests performed on the player. In any case, one or more thresholds may be selected for use with respect to issuing a warning.

Figure 15:
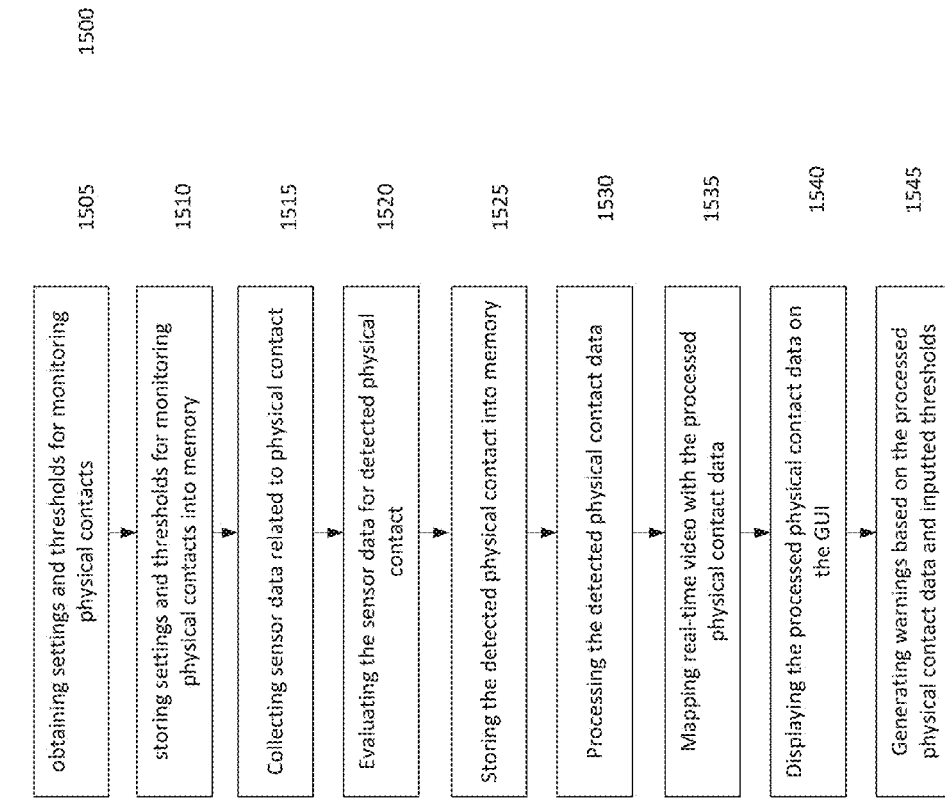
FIG. 15 illustrates a method for monitoring physical contact.

FIG. 15 illustrates a method 1500 for monitoring physical contact. The method is directed at obtaining sensor data from one or more experienced physical contact by a player in-game (e.g., American football) and providing information about the detected physical contact to users (e.g., players, coaches, medical professionals).

In step 1505, the player hit system obtains settings and threshold information that will be used in monitoring the physical contacts for a player within the game. The settings and threshold information, described above, may include information identifying the sensors (e.g., unique sensor identification, location used) being used by the player for detecting the physical contact as well as indicating acceptable levels of physical contact (i.e. thresholds). The settings and threshold information can then be stored in memory in step 1510 for future use with the player hit system.

In step 1515, one or more sensors provide sensor data to the player hit processor. The data provided may be based on the sensors used. For example, motion-based, location-based and health-based sensors may be used to monitor the activities and experiences of a player within the game. In step 1520, the various different sensor data can be evaluated by the player hit processor to determine which groups of sensor data pertains to detected physical contacts. Sensor data concerning physical contact can then be stored in memory in step 1525. Information that is unrelated (i.e. does not identify physical contact) may be identified as such and stored (or alternatively ignored).

The detected physical contact information can then be processed accordingly by the player hit system in step 1530. These processes can identify information such as a total number of hits, total force experienced, and where the physical contact was experienced (e.g., head, arms, legs). The physical contact related information can be associated with recorded in-game video in step 1535. The information and the video may be accessible by the user through the use of the GUI in step 1540. The user can, for example, view the video related to a particular occurrence of a physical contact and compare the information obtained about that physical contact.

Lastly, the player hit system can also provide one or more warnings based on the processed detected physical contact information based on the inputted threshold values in step 1545. It is known that contact sports can cause strain and injury to the body of the player. The warnings are provided as an indicator that the particular player may want to avoid further physical contact as the body may be more susceptible to injury.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claim.

Although the specification and figures may provide various embodiments directed to use of the technology herein within the realm of American football, it should be noted that the technology can be used in a variety of different events and venues including entertainment or cultural events presented at a theater, gymnasium, stadium or other facility involving a group of people. Such events may also include a variety of sporting events such as football (American and global), baseball, basketball, soccer, ice hockey, lacrosse, rugby, cricket, tennis, track and field, golf, cycling, motor sports such as automobile or motorcycle racing, horse racing, Olympic games, and the like; cultural events such as concerts, music festivals, plays, or the opera, and the like; religious events; and more permanent exhibitions such as museums or historic homes.

What is claimed is:

1. A method for monitoring physical contact within a game, the method comprising:
   collecting sensor data for a player participating in the game from a plurality of sensors situated at different locations on the player's body, wherein the collected data from each of the sensors is associated with a respective location of the sensor on the player's body;
   evaluating the collected sensor data for detected physical contact at each of the different locations on the player's body, wherein the evaluation includes:
     detecting instances of physical contact at the location based on the sensor data collected by a respective sensor at the location, wherein the physical contact is detected when accelerometer data from the location indicates a peak that meets a first pre-determined threshold, and wherein conditions other than physical contact are detected when the accelerometer data indicates either no peak or a peak that is less than the first pre-determined threshold, and
     formatting sensor data indicative of physical contact differently from sensor data indicative of conditions other than physical contact;
   and
   displaying the processed detected physical contact data on a graphical user interface (GUI) for a user to view.

2. The method of claim 1 further comprising:
   obtaining threshold information for monitoring physical contact within the game; wherein the threshold information indicates acceptable physical contact that the player can experience within the game; and
   generating a warning based on the processed detected physical contact data being equal to or greater than the threshold information.

3. The method of claim 2, wherein the threshold information pertains to an allowable number of total occurrences of physical contact that can be safely experienced by the player.

4. The method of claim 2, wherein the threshold information pertains to an allowable total amount of force from physical contact that can be safely experienced by the player.

5. The method of claim 2, wherein the threshold information is inputted by the player, coach or medical professional.

6. The method of claim 1 further comprising:
   mapping real-time video with the processed detected physical contact data; and
   displaying the real-time video alongside the processed detected physical contact data in the GUI for the user to view.

7. The method of claim 1, wherein the sensors include motion-based, health-based and location-based sensors.

8. The method of claim 1, wherein the one or more sensors are associated with different parts of the body of the player.

9. The method of claim 8, wherein the different parts of the body of the player includes the head, arms and legs of the player.

10. The method of claim 1, further comprising detecting that at least one of the conditions other than physical contact is running based on the collected sensor data indicating leg movement.

11. A system for monitoring physical contact within a game, the system comprising:
a user interface; and
a processor, the processor executing instructions stored in memory to:
collect sensor data for a player participating in the game from a plurality of sensors situated at different locations on the player's body, wherein the collected data from each of the sensors is associated with a respective location of the sensor on the player's body;
evaluate the collected sensor data for detected physical contact at each of the different locations on the player's body, wherein the evaluation includes:
detecting instances of physical contact at the location based on the sensor data collected by a respective sensor at the location, wherein the physical contact is detected when accelerometer data from the location indicates a peak that meets a first pre-determined threshold, and wherein conditions other than physical contact are detected when the accelerometer data indicates either no peak or a peak that is less than the first pre-determined threshold, and
formatting sensor data indicative of physical contact differently from sensor data indicative of conditions other than physical contact;
and
display the processed detected physical contact data on a graphical user interface (GUI) for a user to view, wherein the GUI is associated with the user interface.

12. The system of claim 11, wherein the processor executes further instructions stored in the memory to:
obtain threshold information for monitoring physical contact within the game; wherein the threshold information indicates acceptable physical contact that the player can experience within the game; and
generate a warning based on the processed detected physical contact data being equal to or greater than the threshold information.

13. The system of claim 12, wherein the threshold information pertains to an allowable number of total occurrences of physical contact that can be safely experienced by the player.

14. The system of claim 12, wherein the threshold information pertains to an allowable total amount of force from physical contact that can be safely experienced by the player.

15. The system of claim 12, wherein the threshold information is inputted by the player, coach or medical professional.

16. The system of claim 11, wherein the processor executes further instructions stored in the memory to:
map real-time video with the processed detected physical contact data; and
display the real-time video alongside the processed detected physical contact data in the GUI for the user to view.

17. The system of claim 11, wherein the sensors include motion-based, health-based and location-based sensors.

18. The system of claim 11, wherein the one or more sensors are associated with different parts of the body of the player.

19. The system of claim 18, wherein the different parts of the body of the player includes the head, arms and legs of the player.

20. A non-transitory computer-readable storage medium, having embodied thereon a program executable by a processor to perform a method for monitoring physical contact within a game, the method comprising:
collecting sensor data for a player participating in the game from a plurality of sensors situated at different locations on the player's body, wherein the collected data from each of the sensors is associated with a respective location of the sensor on the player's body;
evaluating the collected sensor data for detected physical contact at each of the different locations on the player's body, wherein the evaluation includes:
detecting instances of physical contact at the location based on the sensor data collected by a respective sensor at the location, wherein the physical contact is detected when accelerometer data from the location indicates a peak that meets a first pre-determined threshold, and wherein conditions other than physical contact are detected when the accelerometer data indicates either no peak or a peak that is less than the first pre-determined threshold, and
formatting sensor data indicative of physical contact differently from sensor data indicative of conditions other than physical contact; and
displaying the processed detected physical contact data on a graphical user interface (GUI) for a user to view.

* * * * *